(12) United States Patent
Hyun et al.

(10) Patent No.: US 10,064,600 B2
(45) Date of Patent: Sep. 4, 2018

(54) METHOD FOR DISPLAYING ULTRASOUND IMAGE USING DOPPLER DATA AND ULTRASOUND MEDICAL APPARATUS THERETO

(71) Applicant: SAMSUNG MEDISON CO., LTD., Gangwon-do (KR)

(72) Inventors: Dong-gyu Hyun, Gangwon-do (KR); Seok-won Choi, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 499 days.

(21) Appl. No.: 14/052,549

(22) Filed: Oct. 11, 2013

(65) Prior Publication Data
US 2014/0107484 A1    Apr. 17, 2014

(30) Foreign Application Priority Data

Oct. 12, 2012 (KR) .................. 10-2012-0113839
Oct. 31, 2012 (KR) .................. 10-2012-0122571

(51) Int. Cl.
*A61B 8/06*    (2006.01)
*A61B 8/00*    (2006.01)
(Continued)

(52) U.S. Cl.
CPC ............ *A61B 8/463* (2013.01); *A61B 8/06* (2013.01); *A61B 8/13* (2013.01); *A61B 8/461* (2013.01); *A61B 8/466* (2013.01); *A61B 8/467* (2013.01); *A61B 8/483* (2013.01); *A61B 8/488* (2013.01); *A61B 8/5207* (2013.01); *G01S 7/52073* (2013.01); *G01S 15/8984* (2013.01); *G06T 11/206* (2013.01); *A61B 8/0883* (2013.01); *A61B 8/0891* (2013.01); *A61B 8/469* (2013.01);
(Continued)

(58) Field of Classification Search
None
See application file for complete search history.

(56) References Cited

U.S. PATENT DOCUMENTS 6,436,043 B2   8/2002   Bonnefous
7,066,888 B2   6/2006   Abend et al.
(Continued)

FOREIGN PATENT DOCUMENTS

JP    2003517912 A    6/2003
JP    2007-044408 A   2/2007
(Continued)

OTHER PUBLICATIONS

European Search Report issued in European Application No. 13188065.0-1660 dated Feb. 10, 2014.
(Continued)

*Primary Examiner* — Patricia Park
(74) *Attorney, Agent, or Firm* — McDermott Will & Emery LLP

(57) ABSTRACT

Color values of a Doppler image or Doppler data is considered together with a guideline displayed in the Doppler image, and thus a moving direction of a target body may be easily determined. Furthermore, by displaying a marker indicating a moving direction of the target body in the Doppler image, movement of the target body may be easily and efficiently recognized by using the guideline and the marker.

13 Claims, 12 Drawing Sheets

(51) Int. Cl.
- *A61B 8/13* (2006.01)
- *G01S 15/89* (2006.01)
- *G01S 7/52* (2006.01)
- *G06T 11/20* (2006.01)
- *A61B 8/08* (2006.01)

(52) U.S. Cl.
CPC ............ *A61B 8/5223* (2013.01); *A61B 8/565* (2013.01); *A61B 8/585* (2013.01); *G01S 15/8993* (2013.01)

(56) References Cited

U.S. PATENT DOCUMENTS

| | | | |
|---|---|---|---|
| 2002/0151795 A1 | 10/2002 | Palti | |
| 2005/0124885 A1* | 6/2005 | Abend | A61B 8/06 600/443 |
| 2005/0215897 A1 | 9/2005 | Sakaguchi et al. | |
| 2008/0269611 A1 | 10/2008 | Pedrizzetti et al. | |
| 2009/0030321 A1 | 1/2009 | Baba et al. | |
| 2009/0105594 A1* | 4/2009 | Reynolds | A61B 8/06 600/454 |
| 2009/0143667 A1 | 6/2009 | Kovacs et al. | |
| 2009/0315888 A1* | 12/2009 | Brabec | G06T 11/206 345/440 |
| 2010/0069757 A1 | 3/2010 | Yoshikawa et al. | |
| 2011/0196237 A1* | 8/2011 | Pelissier | A61B 8/06 600/454 |
| 2011/0276242 A1* | 11/2011 | O'Dea | B60W 40/10 701/70 |
| 2012/0078106 A1* | 3/2012 | Dentinger | A61B 8/06 600/454 |
| 2013/0041250 A1* | 2/2013 | Pelissier | A61B 8/06 600/424 |
| 2013/0135137 A1* | 5/2013 | Mulder | A61B 5/0507 342/28 |

FOREIGN PATENT DOCUMENTS

| | | |
|---|---|---|
| JP | 2008-073279 A | 4/2008 |
| JP | 4928886 B2 | 5/2012 |

OTHER PUBLICATIONS

Udesen, et al., "Examples of In Vivo Blood Vector Velocity Estimation," Ultrasound in Med. & Biol., vol. 33, No. 4, pp. 541-548, 2007. Elsevier.

Korean Office Action issued in Application No. 10-2012-0122571 dated Jul. 31, 2014.

Korean Notice of Final Rejection issued in corresponding Korean Patent Application No. 10-2012-0122571, dated Feb. 25, 2015; 5 pages with English translation.

Korean Notice of Allowance, issued in corresponding Korean Patent Application No. 10-2012-0122571, dated Mar. 31, 2015; 8 pages with English translation.

\* cited by examiner

METHOD FOR DISPLAYING ULTRASOUND IMAGE USING DOPPLER DATA AND ULTRASOUND MEDICAL APPARATUS THERETO

CROSS-REFERENCE TO RELATED PATENT APPLICATION

This application claims the benefit of Korean Patent Application No. 10-2012-0113839, filed on Oct. 12, 2012 and Korean Patent Application No. 10-2012-0122571, filed on Oct. 31, 2012, in the Korean Intellectual Property Office, the disclosure of which is incorporated herein in its entirety by reference.

BACKGROUND OF THE INVENTION

1. Field of the Invention

The present invention relates to an ultrasound diagnosis of a patient, and more particularly, to a method and an apparatus for efficiently displaying movements of a target body in a Doppler image.

2. Description of the Related Art

An ultrasound diagnosis apparatus generates ultrasound signals (generally 20 kHz or higher) using a probe with respect to a predetermined region in a target body and obtains an image regarding the region in the target body by using data from reflected echo signals. Particularly, an ultrasound diagnosis apparatus is used for medical purposes, e.g., detecting foreign objects in a target body, detecting and observing damages, etc. Since an ultrasound diagnosis apparatus is safe, displays real-time images, and causes no radiation exposure as compared to X-ray, an ultrasound diagnosis apparatus is widely used with other types of imaging diagnosis apparatuses.

An image acquired via an ultrasound diagnosis apparatus (referred to hereinafter as an ultrasound image) may be displayed on the ultrasound diagnosis apparatus or may be stored in a storage medium and displayed on another image display apparatus. For example, an ultrasound image may be displayed at a shrunk size on a mobile phone, a portable electronic device, a personal digital assistant (PDA), or a tablet PC.

Meanwhile, an ultrasound diagnosis apparatus may provide anatomical data according to movement of a target body via a Doppler image. A Doppler image is a gray scale ultrasound image combined with colors based on Doppler data. Therefore, movement of a target body, e.g., flow of blood or movement of a tissue, may be easily viewed in real time.

SUMMARY OF THE INVENTION

The present invention provides a method and an apparatus for displaying an ultrasound image for providing an environment for conveniently and efficiently decoding a Doppler image. The present invention also provides an environment in which a Doppler image may be easily decoded by an image display apparatus other than an ultrasound medical apparatus.

According to an aspect of the present invention, there is provided a method of displaying an ultrasound image, the method including generating a Doppler image from Doppler data regarding a target body; acquiring a guideline regarding at least one from between the Doppler data and the Doppler image; and displaying at least one first marker indicating a moving direction of the target body based on the guideline and the Doppler data.

The method further includes displaying the guideline in the Doppler image.

The acquiring of the guideline includes acquiring the guideline based on a user input for drawing a line in the Doppler image or an automatic detection algorithm stored in advance.

The method further includes determining the moving direction of the target body based on a Doppler direction of the target body, which is determined based on symbolic elements or numeric elements of the Doppler data, and the guideline.

The determining of the moving direction of the target body includes determining a direction, in which the guideline extends and an acute angle is formed between the direction and the Doppler direction, as the moving direction.

The displaying of the at least one first marker includes, if percentage of first markers corresponding to a direction opposite to a first end of the guideline from among the at least one first marker is below or equal to a predetermined percentage, displaying the first markers corresponding to the direction opposite to the first end of the guideline to indicate the direction toward the first end of the guideline.

The displaying of the at least one first marker includes, if percentage of first markers corresponding to a direction opposite to a first end of the guideline from among the at least one first marker is below or equal to a predetermined percentage, displaying a second marker at a location of a first marker indicating the opposite direction to the direction toward the first end of a guideline The displaying of the at least one first marker includes, if it is unable to determine the moving direction of the target body based on the guideline and the Doppler data, displaying a third marker indicating that the moving direction of the target body is not determined.

The determining of the moving direction of the target body includes determining the moving direction of the target body based on statistical functions regarding at least one from among the Doppler direction, a moving speed of the target body, amplitudes of Doppler signals, power of the Doppler signals, and distances to nearby spaces.

The statistical function is a function using Doppler data of a nearby space to a location at which the moving direction of the target body is to be determined.

The displaying of the first marker includes displaying the at least one first marker along the guideline.

The displaying of the first marker includes displaying the at least one first marker at a predetermined interval.

The displaying of the first marker includes displaying the first marker at a first end of the guideline.

The Doppler image includes at least one of blood flow Doppler image showing flow of blood and a tissue Doppler image showing movement of a tissue.

The Doppler data includes 2D Doppler data or 3D Doppler data.

The displaying of the first marker includes 2-dimensionally rendering or 3-dimensionally rendering the first marker and displaying the rendered first marker.

The acquiring of the guideline based on an automatic detection algorithm includes specifying a region including information regarding movement of the target body in the Doppler image; and acquiring the guideline from the specified region.

The displaying of the first marker includes displaying the first marker after changing at least one from among length, size, width, contrast, and color of the first marker, based on the Doppler data.

According to another aspect of the present invention, there is provided an ultrasound medical apparatus including an image processing unit, which generates a Doppler image from Doppler data regarding a target body and acquires a guideline regarding at least one of the Doppler data and the Doppler image; and a display unit, which displays at least one first marker indicating a moving direction of the target body based on the guideline and the Doppler data.

According to another aspect of the present invention, there is provided a method of displaying an ultrasound image, the method including generating a Doppler image from Doppler data received from outside; acquiring a guideline regarding at least one from between the Doppler data and the Doppler image; and displaying at least one first marker indicating a moving direction of the target body based on the guideline and the Doppler data.

According to another aspect of the present invention, there is provided an ultrasound medical apparatus including an image processing unit, which generates a Doppler image from Doppler data received from outside and acquires a guideline regarding at least one of the Doppler data and the Doppler image; and a display unit, which displays at least one first marker indicating a moving direction of the target body based on the guideline and the Doppler data.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

In addition, although the terms used in the present invention are selected from generally known and used terms, some of the terms mentioned in the description of the present invention have been selected by the applicant at his or her discretion, the detailed meanings of which are described in relevant parts of the description herein. Furthermore, it is required that the present invention is understood, not simply by the actual terms used but by the meaning of each term lying within.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, the term "target body" may denote a patient for ultrasound diagnosis. However, the term "target body" is not limited to the entire patient and may also denote a portion of the patient; e.g., a predetermined region, a predetermined tissue, or blood. In other words, the term "target body" may denote a predetermined region which reflects emitted ultrasound signals.

Hereinafter, exemplary embodiments of the present invention will be described in detail with reference to the attached drawings.

Figure 1:
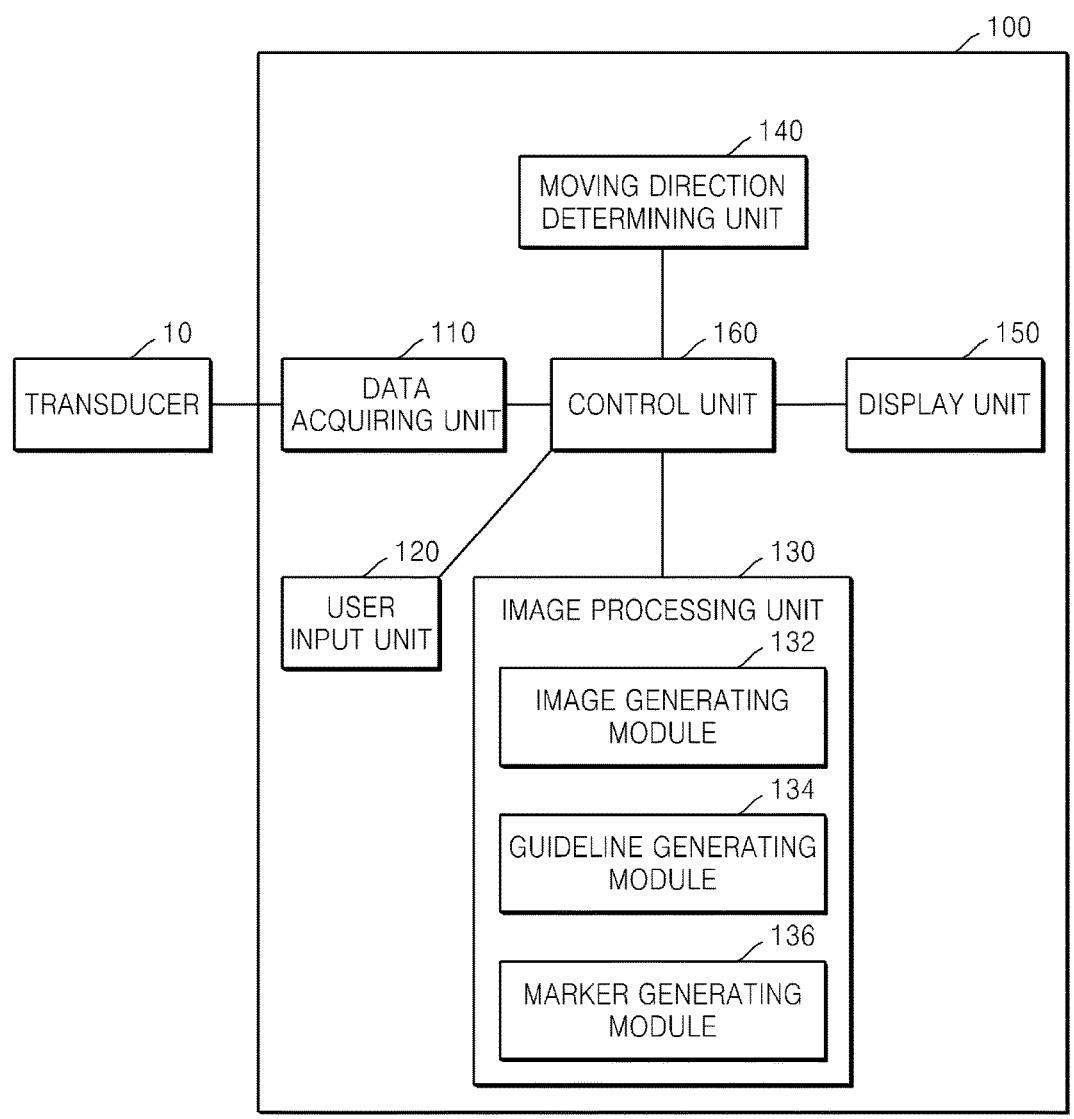
FIG. 1 is a block diagram showing the configuration of an ultrasound medical apparatus according to an embodiment of the present invention.

FIG. 1 is a block diagram showing the configuration of an ultrasound medical apparatus 100 according to an embodiment of the present invention. The ultrasound medical apparatus 100 according to the present embodiment may include a transducer 10, a data acquiring unit 110, a user input unit 120, an image processing unit 130, a moving direction determining unit 140, a display unit 150, and a control unit 160. The configuration shown in FIG. 1 regarding the ultrasound medical apparatus 100 is merely an embodiment, and the ultrasound medical apparatus 100 may further include general purpose components other than the components shown in FIG. 1.

The ultrasound medical apparatus 100 scans a target body and generates an ultrasound image. In other words, the ultrasound medical apparatus 100 emits ultrasound signals to a target body via the transducer 10, receives echo signals reflected by the target body, and generates an ultrasound image using the echo signals. An ultrasound image generated by the ultrasound medical apparatus 100 may include not only a 2-dimensional image showing sectional image of a target body, but also 3-dimensional volume data.

Furthermore, the ultrasound medical apparatus 100 may generate not only a gray scale ultrasound image obtained by scanning a target body in an amplitude (A) mode, a brightness (B) mode, or a motion (M) mode, but also a Doppler image showing movement of the target body based on color information of Doppler data. A Doppler image generated by the ultrasound medical apparatus 100 may include at least one of a blood flow Doppler image showing flow of blood (or a color Doppler image) and a tissue Doppler image showing movement of a tissue.

Meanwhile, the ultrasound medical apparatus 100 may not only autonomously acquire an ultrasound image by using the transducer 10, but also receive an ultrasound image and Doppler data from an external device via a wired or wireless network. For example, the ultrasound medical apparatus 100 may receive various types of data, such as an ultrasound image and Doppler data, from another device within a hospital server via a picture archiving and communication system (PACS). Alternatively, the ultrasound medical apparatus 100 may also include a workstation or a PACS viewer, which displays and processes an ultrasound image but does not generate an ultrasound image.

The data acquiring unit 110 acquires echo signals for generating an ultrasound image from the transducer 10. Furthermore, the data acquiring unit 110 also acquires Doppler data from a target body. In other words, the data acquiring unit 110 may acquire Doppler data indicating movement of the target body by analyzing echo signals received via the transducer 10 and emitted ultrasound signals. Doppler data acquired by the data acquiring unit 110 may include information regarding a moving direction of the target body. Furthermore, the Doppler data may further include information regarding at least one of an amplitude of a Doppler signal that is determined based on a difference between frequency of an emitted ultrasound signal and frequency of an echo signal and a velocity at which the target body moves.

Furthermore, according to forms of echo signals received by the transducer 10, Doppler data acquired by the data acquiring unit 110 may further include not only planar-spatial Doppler (2D Doppler) data, but also stereoscopic-spatial Doppler (3D Doppler) data.

Furthermore, Doppler data acquired by the data acquiring unit 110 may include not only Doppler data regarding a still image, but also Doppler data regarding successive images, such as a moving image.

The user input unit 120 receives external input signals for controlling the ultrasound medical apparatus 100 from a user. In other words, the user input unit 120 may receive not only user inputs via various types of input devices, such as a keypad, a mouse, and a trackball, but also touch inputs via a touch screen and user inputs via a remote control device.

Meanwhile, the user inputs received by the user input unit 120 may include various types of inputs. For example, the user input unit 120 may receive a guideline input for drawing a guideline from a user. Alternatively, the user input unit 120 may receive a user input for controlling interval between two or more first markers.

The image processing unit 130 generates an ultrasound image obtained by scanning a target body and various information to be displayed on the display unit 150. In detail, the image processing unit 130 may include a image generating module 132 which generates an ultrasound image by using echo signals, a guideline generating module 134 which generates a guideline, and a marker generating module 136 which generates various types of markers. Detailed descriptions thereof will be given below.

Meanwhile, the image processing unit 130 may render an ultrasound image and a marker. In other words, the image processing unit 130 may 2-dimensionally or 3-dimensionally render an ultrasound image, a guideline, and markers that are respectively generated by the image generating module 132, guideline generating module 134, and the marker generating module 136.

The guideline generating module 134 may generate not only a gray scale ultrasound image, but also a color Doppler image. In other words, the image processing unit 130 may generate a Doppler image by using a color map in which movements of a target body are matched to colors. Furthermore, the image generating module 132 may generate not only a 2-dimensional image showing sectional image of a target body, but also 3-dimensional volume data The guideline generating module 134 generates a guideline according to a user input or via an automatic detection algorithm that is stored in a system in advance. In other words, the guideline generating module 134 may receive a user input corresponding to a straight line or a curved line drawn by a user and generate a guideline based on the received input. Furthermore, the guideline generating module 134 may automatically generate a guideline by applying a predetermined algorithm to a Doppler image.

The detailed description of an embodiment in which the guideline generating module 134 acquires a guideline of a Doppler image by using an existing automatic detection algorithm will be given below with reference to FIG. 14.

Meanwhile, the guideline generating module 134 may acquire a guideline regarding at least one of Doppler data and a Doppler image. In other words, the guideline generating module 134 may acquire a guideline from Doppler data acquired by processing echo signals received from a target body or acquire a guideline by analyzing a Doppler image which visualizes Doppler data. Furthermore, the guideline generating module 134 may acquire a guideline using both Doppler data and a Doppler image. According to an embodiment of the present invention, the guideline generating module 134 may acquire a guideline by applying an automatic detection algorithm to Doppler data or acquire a guideline based on a user input regarding a Doppler image.

The guideline generating module 134 may generate not only a guideline regarding a 2D plane, but also a 3D guideline displayed in a 3D ultrasound image. A 3D guideline may refer to a line displayed in a 3D space.

The marker generating module 136 generates various types of markers indicating information regarding an ultrasound image. For example, the marker generating module 136 may generate a first marker indicating a moving direction of a target body, a second marker indicating an inconsistent direction, a third marker indicating that moving direction is not determined, etc. Furthermore, the marker generating module 136 may display a 3D marker displayed in a 3D ultrasound image. Unlike a marker indicating a particular direction on a 2D plane, a 3D marker may indicate a direction in a 3D space.

According to an embodiment of the present invention, the marker generating module 136 may generate markers by changing forms of markers by using information included in Doppler data regarding a moving direction of a target body, a moving speed of the target body, and amplitudes of Doppler signals. For example, the marker generating module 136 may generate markers in various forms by changing at least one from among lengths, sizes, widths, contrasts, and colors of markers to be generated, based on various information included in Doppler data.

The moving direction determining unit 140 determines a moving direction of a target body, that is, a moving direction of the target body. In other words, the moving direction determining unit 140 may determine a moving direction of a target body by analyzing Doppler data. For example, the moving direction determining unit 140 may determine a moving direction by using symbolic elements or numeric elements included in Doppler data. Meanwhile, a "moving direction" of a target body may refer to a moving direction of the target body when a ultrasound signal emitted by the transducer 10 is reflected by the target body.

Hereinafter, a process in which the moving direction determining unit 140 determines a moving direction will be described in detail. The moving direction determining unit 140 may determine a Doppler direction based on Doppler data. A Doppler direction may be a moving direction of a target body away from the transducer 10 or a moving direction of the target body toward the transducer 10. In other words, the moving direction determining unit 140 may determine a moving direction of a target body away from the transducer 10 (referred to hereinafter as a first direction) or a moving direction of the target body toward the transducer 10 (referred to hereinafter as a second direction) as a Doppler direction based on a symbolic element included in Doppler data, e.g., "+" or "−".

Furthermore, the moving direction determining unit 140 may determine a Doppler direction by using a numeric element included in Doppler data, e.g., a value from 0 to 255. In detail, the moving direction determining unit 140 may determine the first direction as the Doppler direction regarding values from 0 to 127 and may determine the second direction as the Doppler direction regarding values form 128 to 255 (or vice versa).

Next, the moving direction determining unit 140 may determine a moving direction of a target body based on the determined Doppler direction and a guideline. According to an embodiment of the present invention, the moving direction determining unit 140 may determine a moving direction by using an angle formed between a Doppler direction and a guideline. In detail, a direction, in which the guideline extends and an acute angle is formed between the direction and the Doppler direction, may be determined as the moving direction. Detailed descriptions thereof will be given below with reference to FIG. 8.

Furthermore, the moving direction determining unit 140 may acquire not only a Doppler direction of a target body, but also at least one of information regarding moving speed of the target body, amplitude of a Doppler signal, and power of the Doppler signal. In other words, the moving direction determining unit 140 may also determine amplitude of a Doppler signal corresponding to a Doppler frequency that is determined based on a difference between frequencies of an emitted ultrasound signal and a received echo signal and a speed at which a target body moves, based on the Doppler data. In other words, the moving direction determining unit 140 may acquire and determine various types of information regarding movement of a target body based on Doppler data.

Meanwhile, according to an embodiment of the present invention, the moving direction determining unit 140 may use Doppler data regarding space surrounding a target body for determining a moving direction of the target body. In other words, the moving direction determining unit 140 may determine a moving direction of the target body in consideration of not only Doppler data regarding the target body, but also Doppler data regarding surrounding space nearby the target body (e.g., symbolic elements or numeric components). For a 2D Doppler data, the moving direction determining unit 140 may consider Doppler data regarding 4 directions (up, down, left, and right) or 8 directions including the 4 directions and diagonal directions, nearby an arbitrary location. For a 3D Doppler data, the moving direction determining unit 140 may consider Doppler data regarding 6 directions (up, down, left, right, front, and rear) or 26 directions including the 6 directions and diagonal directions, nearby an arbitrary location.

Here, the moving direction determining unit 140 may use a predetermined statistical functions stored in the ultrasound medical apparatus 100. For example, the moving direction determining unit 140 may use any of various functions including sum, weighted sum, average, variance, etc. For example, in case of weighted sum, the moving direction determining unit 140 may determine symbols according to a direction corresponding to a value obtained by multiplying Doppler data of a surrounding space by at least one of amplitude of a Doppler signal and Doppler speed and sum the symbols.

The display unit 150 displays various images and information generated by the image processing unit 130. For example, the display unit 150 may display various types of data including a 2D ultrasound image, a 3D ultrasound image, a Doppler image, a guideline, and a marker.

The display unit 150 may display various types of information for indicating movement of a target body. In other words, the display unit 150 may display a Doppler image and may overlay data indicating movement of a target body, such as a first marker and a guideline, on the Doppler image.

According to an embodiment of the present invention, to indicate a moving direction of a target body by using first markers, the display unit 150 may display the first markers along a guideline. In other words, the display unit 150 may display one or more first markers indicating a moving direction of a target body on a guideline in a Doppler image. For example, the display unit 150 may either display a plurality of first markers or display one first marker at an end of a guideline. Meanwhile, the display unit 150 may indicate a moving direction of a target body by displaying only first markers without a guideline.

Furthermore, the display unit 150 may display the plurality of first markers at a predetermined interval, where the interval may be adjusted based on a user input or automatically by a system. Various embodiments for the display unit 150 to display first markers, second markers, and third markers will be described below in detail with reference to FIGS. 9 and 10.

Meanwhile, the display unit 150 may include at least one from among a liquid crystal display, a thin-film transistor liquid crystal display, an organic light-emitting diode, a flexible display, and a 3D display. Furthermore, the ultrasound medical apparatus 100 may include the two or more display units 150.

According to an embodiment of the present invention, the display unit 150 may include a touch screen that forms a layered structure together with the user input unit 120 for receiving external inputs. In other words, the display unit 150 may be used both as an input device and an output device. Here, the display unit 150 may receive touch inputs made by using a stylus pen or a body part.

Furthermore, as described above, if the display unit 150 forms a layered structure as a touch screen, the display unit 150 may detect a touch input location, a touch input area, and a touch pressure. Furthermore, the touch screen may detect not only a real touch, but also a proximity touch.

The control unit 160 controls overall components included in the ultrasound medical apparatus 100. In other words, the control unit 160 may control the moving direction determining unit 140 to determine a moving direction of a target body by using Doppler data acquired by the data acquiring unit 110. Furthermore, the control unit 160 may control the image processing unit 130 to generate a guideline based on a user input received by the user input unit 120 or may control the display unit 150 to display generated markers.

Figure 2:
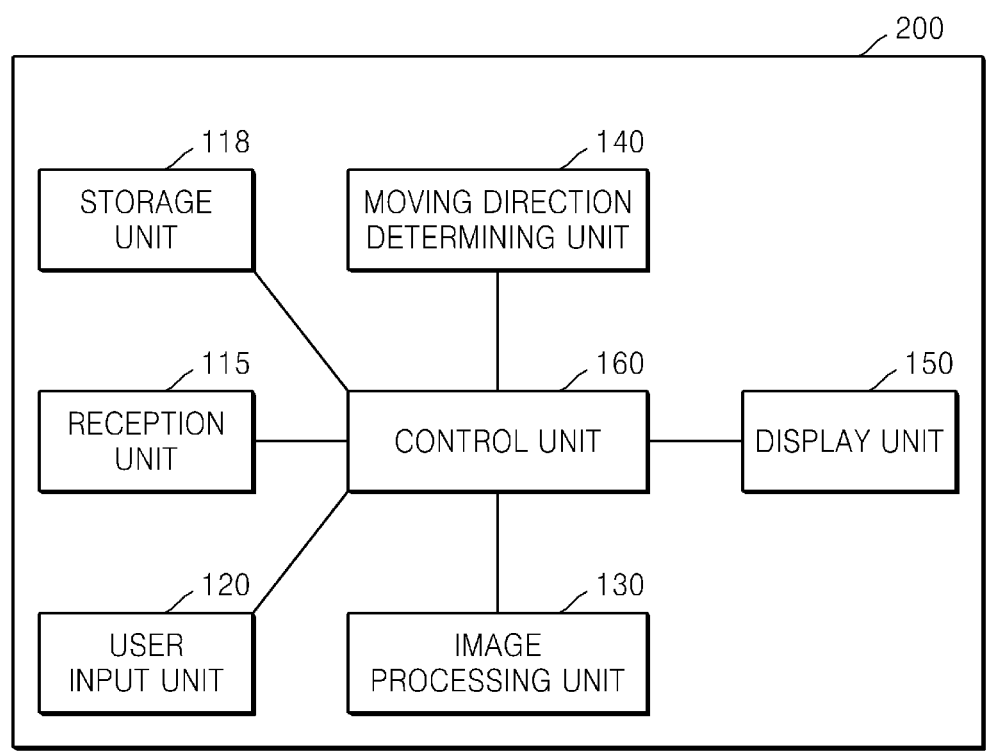
FIG. 2 is a block diagram showing the configuration of an image display apparatus according to an embodiment of the present invention.

FIG. 2 is a block diagram showing the configuration of an image display apparatus 200 according to an embodiment of the present invention. The image display apparatus 200 according to the present embodiment may include a reception unit 115, a storage unit 118, the user input unit 120, the image processing unit 130, the moving direction determining unit 140, the display unit 150, and the control unit 160. The configuration of the image display apparatus 200 shown in FIG. 2 is merely an example, and the image display apparatus 200 may further include general purpose components other than the components shown in FIG. 2.

Hereinafter, the components included in the image display apparatus 200 will be described. Meanwhile, any of descriptions regarding the user input unit 120, the image processing unit 130, the moving direction determining unit 140, the display unit 150, and the control unit 160 that are already given above with reference to FIG. 1 will be omitted.

The image display apparatus 200 is any of various types of devices including the display unit 150 for displaying ultrasound images. In other words, unlike the ultrasound medical apparatus 100 shown in FIG. 1, the image display apparatus 200 shown in FIG. 2 does not emit ultrasound signals or generate ultrasound images. Instead, the image display apparatus 200 may acquire ultrasound images and Doppler data via a network or from an external device and display the ultrasound images and the Doppler data.

Therefore, the image display apparatus 200 may be embodied in any of various forms for displaying ultrasound images (including Doppler images) on the display unit 150. For example, the image display apparatus 200 may be embodied in any of various forms including a mobile phone, a smart phone, a smart TV, an internet protocol TV (IPTV), a digital TV (DTV), a personal computer (PC), a laptop computer, a tablet PC, an e-book reader, a personal digital assistant (PDA), a portable multimedia player (PMP), a navigation device, a consumer electronic (CE) device (e.g., a refrigerator or an air conditioner including a display panel), etc. As described above with reference to FIG. 1, the image display apparatus 200 may also be a workstation or a fax viewer, which only processes ultrasound images without generating the same.

The reception unit 115 receives Doppler data or a Doppler image generated by an external device. In other words, the reception unit 115 may acquire Doppler data or a Doppler image via a wired network or a wireless network. For example, the reception unit 115 may acquire a Doppler image or Doppler data from an external device, a server, or a cloud server via a wired connection, such as USB and data cable, or a wireless connection, such as Bluetooth, near field communication (NFC), Wi-Fi, and 2G/3G/4G networks. A Doppler image and Doppler data acquired by the reception unit 115 are stored in the storage unit 118.

Furthermore, the reception unit 115 may acquire a Doppler image and Doppler data together. In other words, unlike the ultrasound medical apparatus 100 described above with reference to FIG. 1, the image display apparatus 200 does not scan a target body by itself. However, the image display apparatus 200 may receive and acquire Doppler data and a Doppler image generated by an external device via a wired connection or a wireless connection.

As described above with reference to FIG. 1, the moving direction determining unit 140 determines a moving direction of a target body displayed in a Doppler image. In other words, the moving direction determining unit 140 may determine a moving direction of a target body by loading and analyzing a Doppler image stored in the storage unit 118.

Meanwhile, the moving direction determining unit 140 of FIG. 2 may determine a moving direction of a target body by using color information of a Doppler image. In other words, since the moving direction determining unit 140 included in the image display apparatus 200 of FIG. 2 does not acquire Doppler data by itself, the moving direction determining unit 140 may determine a moving direction of a target body based on color values of a Doppler image. In other words, the moving direction determining unit 140 may determine a Doppler direction based on values of colors displayed in a Doppler image instead of symbolic elements or numeric elements of Doppler data and may determine a moving direction of a target body by using the Doppler direction determined based on color values and a guideline.

For example, if values of colors displayed in a Doppler image are within a predetermined range (e.g., a predetermined range indicating blue colors), the moving direction determining unit 140 may determine Doppler direction of a target body as a first direction, which is a direction away from a probe. On the contrary, if values of colors displayed in a Doppler image are within another predetermined range (e.g., a predetermined range indicating red colors), the moving direction determining unit 140 may determine Doppler direction of a target body as a seocn direction, which is a direction toward a probe.

Meanwhile, the moving direction determining unit 140 may determine a Doppler direction by analyzing not only colors of a Doppler image, but also Doppler data externally acquired by the reception unit 115. In other words, the moving direction determining unit 140 may determine a Doppler direction based on at least one of color information and Doppler data. The moving direction determining unit 140 of the image display apparatus 200 determines a Doppler direction by suing Doppler data in the same manner as described above regarding the ultrasound medical apparatus 100 of FIG. 1.

Furthermore, similar to the description given above with reference to FIG. 1, the moving direction determining unit 140 of the image display apparatus 200 may determine a Doppler direction based on statistical functions regarding at least one from among colors, chroma, and brightness of a Doppler image.

When a Doppler direction is determined, the moving direction determining unit 140 may determine a moving direction of a target body based on the Doppler direction and a guideline. In other words, as described above with reference to FIG. 1, the moving direction determining unit 140 may determine a moving direction of a target body by using a determined Doppler direction and a guideline.

The control unit 160 shown in FIG. 2 may control not only the user input unit 120, the image processing unit 130, the moving direction determining unit 140, and the display unit 150, but also the reception unit 115 and the storage unit 118. In other words, the control unit 160 may control the storage unit 118 to store a Doppler image acquired by the reception unit 115. Furthermore, the control unit 160 may control the moving direction determining unit 140 to analyze a Doppler image stored in the storage unit 118.

Descriptions given above are related to the image display apparatus 200 for receiving a Doppler image and processing color information. However, according to an embodiment of the present invention, the image display apparatus 200 may receive and process Doppler data. For example, if the image display apparatus 200 includes a fax viewer, which is a non-medical device capable of receiving and processing Doppler data, the image display apparatus 200 may receive Doppler data via the reception unit 115 and process the Doppler data via the moving direction determining unit 140, thereby determining a moving direction of a target body.

In other words, the image display apparatus 200 according to the present embodiment may operate similarly as the ultrasound medical apparatus 100 of FIG. 1 which externally receives and processes Doppler data. In other words, the image display apparatus 200 may receive Doppler data, generate a Doppler image, and display markers indicating a moving direction of a target body displayed in the Doppler image.

Hereinafter, a method of displaying images by using the configurations of the ultrasound medical apparatus 100 and the image display apparatus 200 shown in FIGS. 1 and 2 will be described with reference to FIGS. 3 through 5.

Figure 3:
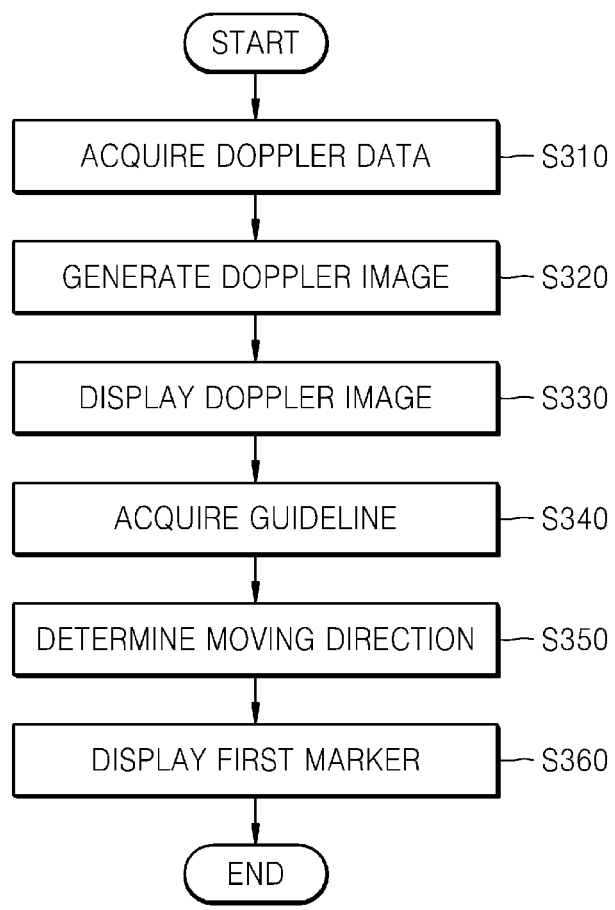
FIG. 3 is a flowchart for describing a method of displaying an ultrasound image according to an embodiment of the present invention.

FIG. 3 is a flowchart for describing a method of displaying an ultrasound image according to an embodiment of the present invention. The flowchart shown in FIG. 3 includes operations that are carried out by the ultrasound medical apparatus 100, the transducer 10, the data acquiring unit 110, the user input unit 120, the image processing unit 130, the moving direction determining unit 140, the display unit 150, and the control unit 160 in chronological order. Therefore, even if omitted below, any of descriptions given above regarding the configuration of FIG. 1 may also be applied to the flowchart shown in FIG. 3.

In an operation S310, the ultrasound medical apparatus 100 acquires Doppler data. In other words, the ultrasound medical apparatus 100 may acquire Doppler data for generating a Doppler image by emitting ultrasound signals to a target body and receiving echo signals from the target body. As described above, the Doppler data may include information regarding at least one from among moving direction of a target body, moving speed of the target body, and amplitude of a Doppler signal.

In an operation S320, the ultrasound medical apparatus 100 generates a Doppler image. In other words, the ultrasound medical apparatus 100 may generate a Doppler image which displays movement of a target body by using colors in a gray scale ultrasound image, based on the Doppler data received in the operation S310. Meanwhile, in the operation S320, the ultrasound medical apparatus 100 may generate only a gray scale ultrasound image based on echo signals.

In an operation S320, the ultrasound medical apparatus 100 displays the Doppler image generated in the operation S320. In other words, the ultrasound medical apparatus 100 may display an ultrasound image and a Doppler image using color values. A Doppler image may include 2D volume data regarding cross-section of a target body or 3D volume data.

In an operation S340, the ultrasound medical apparatus 100 acquires a guideline. In other words, the ultrasound medical apparatus 100 may acquire a guideline based on an user input received from outside or an automatic detection algorithm stored in advance. For example, the ultrasound medical apparatus 100 may receive a user input which forms any of various shapes, such as a straight line, a curved line, and a closed-loop, via a trackball, a mouse, or a touch screen and generate a guideline based on the user input.

For another example, the ultrasound medical apparatus 100 may acquire or generate a guideline by using a CCA algorithm or a skeletonization algorithm. Detailed description of embodiments in which the ultrasound medical apparatus 100 uses automatic detection algorithms will be given below with reference to FIG. 14.

Meanwhile, in an operation S340, the ultrasound medical apparatus 100 may display a guideline generated based on an user input or an automatic detection algorithm on a screen.

In an operation S350, the ultrasound medical apparatus 100 determines a direction in which a target body moves, that is, a moving direction of the target body. In other words, the ultrasound medical apparatus 100 may determine a moving direction of a target body based on the guideline acquired in the operation S340 and the Doppler data acquired in the operation S310.

In detail, the ultrasound medical apparatus 100 may determine a Doppler direction indicating whether a target body is moving away from a probe or moving toward the probe, by using symbolic elements or numeric elements of Doppler data and may determine a moving direction of the target body based on the Doppler direction and the guideline.

According to an embodiment of the present invention, the ultrasound medical apparatus 100 may determine a direction, in which the guideline extends and an acute angle is formed between the direction and the Doppler direction, as the moving direction. Detailed descriptions thereof will be given below with reference to FIG. 8.

Meanwhile, in the operation S350, the ultrasound medical apparatus 100 may determine the moving direction by using any of various statistical functions regarding one or more factors included in the Doppler data. In other words, the ultrasound medical apparatus 100 may use any of various functions including sum, weighted sum, average, variance, etc. for determining the moving direction of the target body. Meanwhile, the statistical function may be a function using Doppler data regarding a space that is 2-dimensionally or 3-dimensionally closed to an arbitrary location. In other words, to determine a moving direction of a target body regarding an arbitrary location, the ultrasound medical apparatus 100 may use not only Doppler data regarding the corresponding location, but also statistical functions based on Doppler data regarding a plurality of locations spatially nearby the corresponding location.

In an operation S360, the ultrasound medical apparatus 100 displays a first marker indicating the moving direction of the target body. In other words, the ultrasound medical apparatus 100 may display the moving direction of the target body by displaying at least one first marker. In the operation S360, the ultrasound medical apparatus 100 may display not only a 2D marker, but also a 3D marker regarding 3D volume data via a 3D rendering operation.

According to an embodiment of the present invention, the ultrasound medical apparatus 100 may display at least one first marker along a guideline at a predetermined interval or only one first marker at a first end of a guideline.

According to another embodiment of the present invention, the ultrasound medical apparatus 100 may determine percentage of first markers corresponding to a direction opposite to the first end of the guideline of the operation S350 from among the at least one first marker and may modify and display first markers based on the percentage. Detailed description thereof will be given below with reference to FIG. 4.

Figure 4:
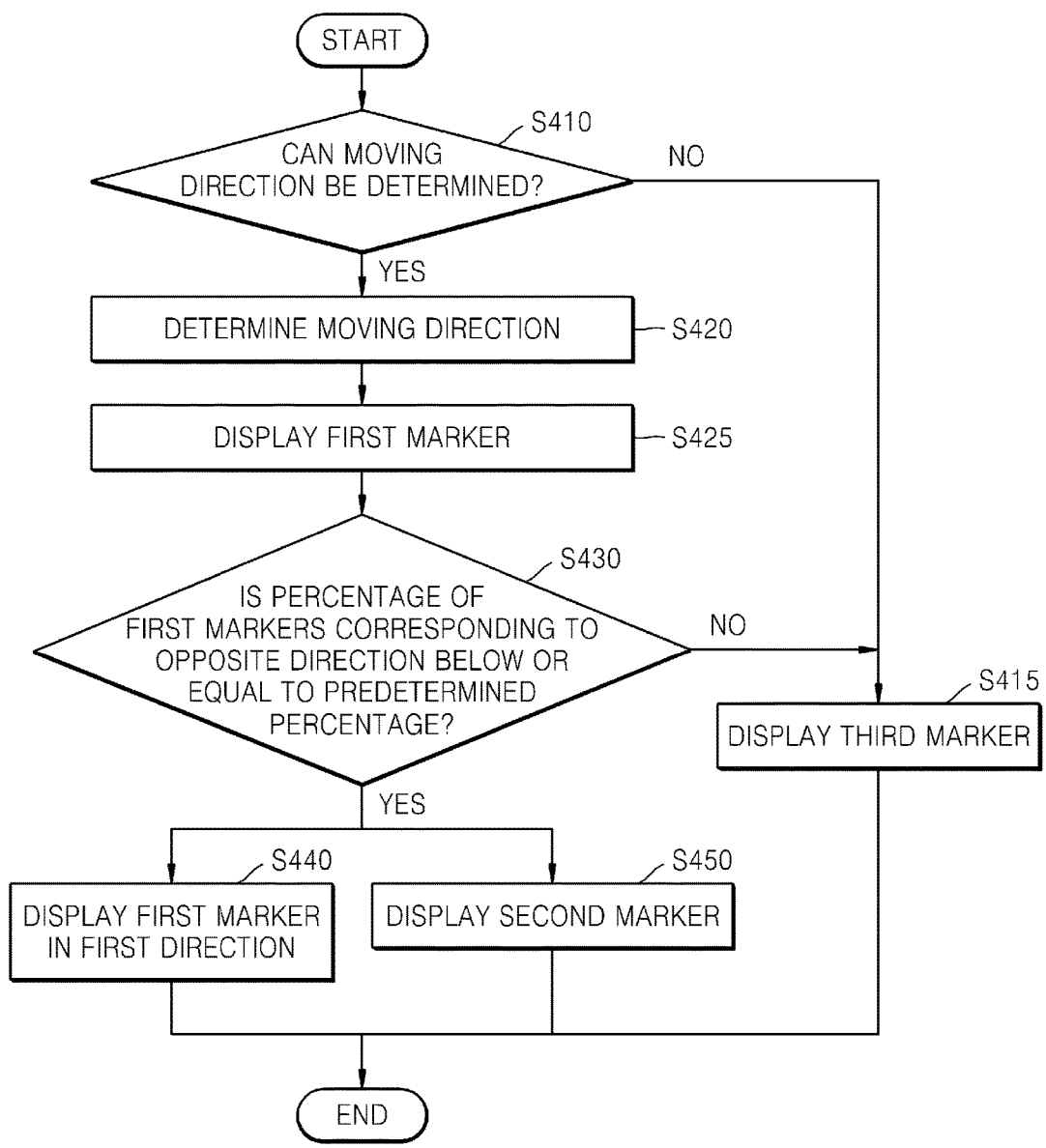
FIG. 4 is a flowchart for describing a method of displaying an ultrasound image according to another embodiment of the present invention.

FIG. 4 is a flowchart for describing a method of displaying an ultrasound image according to another embodiment of the present invention. The flowchart shown in FIG. 4 includes operations after the operation S340 of FIG. 3.

In an operation S410, the ultrasound medical apparatus 100 determines whether a moving direction of a target body may be determined. In other words, the ultrasound medical apparatus 100 determines whether it is a situation in which it is unable to determine a moving direction of a target body by using Doppler data and a guideline. For example, it is unable to determine a moving direction of a target body in a case where a target area is a gray scale area in which no Doppler data exists, a case where, since a target body moves in a direction perpendicular to a moving direction of the transducer 10 (that is, a direction corresponding to Doppler direction of 90 degrees), no Doppler data exists, and a case where a target area is an area showing irregular movements, such as turbulence. If it is unable to determine a moving direction of a target body, the overall process proceeds to an operation S415. If a moving direction of a target body may be determined, the overall process proceeds to an operation S420.

In the operation S415, the ultrasound medical apparatus 100 displays a third marker indicating that a moving direction of a target body is not determined. In other words, the ultrasound medical apparatus 100 may display the third marker which indicates that determination is deferred regarding a corresponding location. According to an embodiment of the present invention, the third marker may have a "X"-like shape.

In the operation S420, the ultrasound medical apparatus 100 determines a moving direction of a target body. In other words, as in the operation S350 of FIG. 3, the ultrasound medical apparatus 100 determines the moving direction of the target body based on Doppler data and a guideline.

Next, in an operation S425, the ultrasound medical apparatus 100 may display at least one first marker indicating the determined moving direction. The ultrasound medical apparatus 100 may display first markers along a guideline at a predetermined interval. According to an embodiment of the present invention, the ultrasound medical apparatus 100 may display at least one first marker toward a first end of the guideline.

In an operation S430, the ultrasound medical apparatus 100 determines whether percentage of first markers corresponding to a direction opposite to the first end of the guideline from among the at least one first marker is below or equal to a predetermined percentage. In detail, from among the at least one first marker displayed along the guideline, the ultrasound medical apparatus 100 may include one or more first markers indicating a direction that is not identical to the direction toward the first end of the guideline, that is, a direction opposite to the direction toward the first end of the guideline.

Accordingly, the ultrasound medical apparatus 100 may determine percentage of a plurality of first markers corresponding to a direction opposite to the first end of the guideline from among the at least one first marker indicating and may modify. For example, 95% of the first markers may indicate the direction toward the first end of the guideline, whereas 5% of the first markers may indicate the opposite direction.

In the operation S430, the ultrasound medical apparatus 100 determines percentage of the first markers indicating the opposite direction and, if the corresponding percentage is below or equal to a predetermined value, the overall process proceeds to an operation S440 or an operation S450. If the corresponding percentage exceeds the predetermined value, the overall process proceeds to the operation S415, and the ultrasound medical apparatus 100 may display a third marker indicating that a moving direction of a target body is not determined, instead of at least one first marker.

Meanwhile, the ultrasound medical apparatus 100 may adjust percentage of first markers indicating the opposite direction based on a user input or automatically by a system. In other words, if a target body appears in a Doppler image in a manner that Doppler direction frequently crosses, the ultrasound medical apparatus 100 may increase percentage of the first markers indicating the opposite direction. In other words, the ultrasound medical apparatus 100 may display the moving direction determined in the operation S420 without displaying a third marker.

Meanwhile, operations S440 and S450 may be carried out based on values set by a user. In other words, if it is set to force first markers indicating the opposite direction to indicate the direction toward the first end of a guideline, the overall process proceeds to the operation S440. If it is set to display the first markers indicating the opposite direction separately as second markers, the overall process proceeds to the operation S450.

In the operation S440, the ultrasound medical apparatus 100 modifies and displays first markers indicating the opposite direction to the direction toward the first end of a guideline to indicate the direction toward the first end of the guideline. In other words, the ultrasound medical apparatus 100 may display all of the first markers to indicate a same direction by modifying a part of the first markers below or equal to a predetermined percentage in the operation S430.

In the operation S450, the ultrasound medical apparatus 100 may display a second marker at a location of a first marker indicating the opposite direction to the direction toward the first end of a guideline. Therefore, a user of the ultrasound medical apparatus 100 may passively recognize a relationship between a Doppler image and a guideline, and thus the user may diagnose a target body accurately with clinical information.

Figure 5:
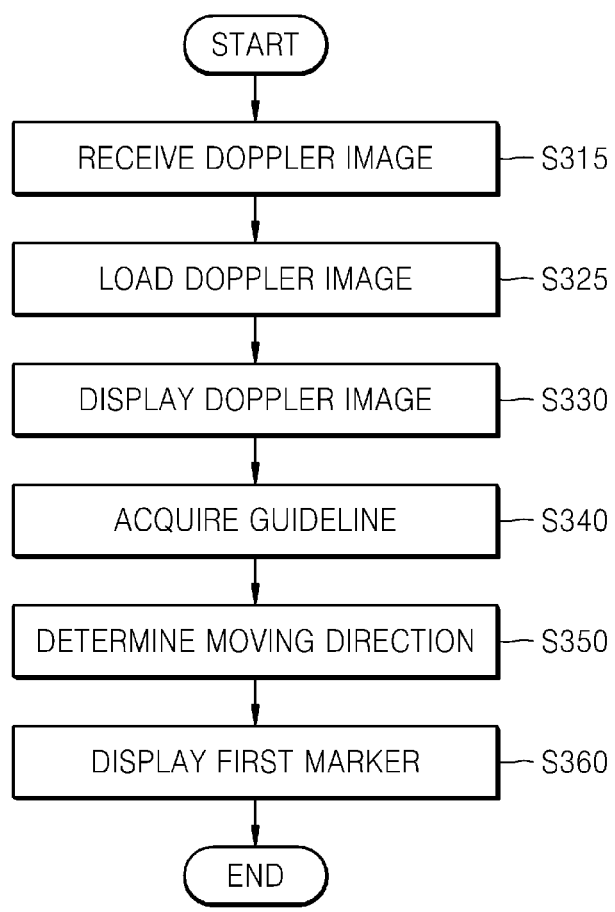
FIG. 5 is a flowchart showing a method of displaying an image according to an embodiment of the present invention.

FIG. 5 is a flowchart showing a method of displaying an image according to an embodiment of the present invention. The flowchart shown in FIG. 5 includes operations that are carried out by the image display apparatus 200, the reception unit 115, the storage unit 118, the user input unit 120, the image processing unit 130, the moving direction determining unit 140, the display unit 150, and the control unit 160 in chronological order. Therefore, even if omitted below, any of descriptions given above regarding the configuration of FIG. 2 may also be applied to the flowchart shown in FIG. 5. Meanwhile, any of descriptions that are already given above with reference to FIGS. 3 and 4 will be omitted below.

In an operation S315, the image display apparatus 200 receives a Doppler image. In other words, the image display apparatus 200 receives a Doppler image from at least one from among an external device, a hospital server, and a cloud server via a wired network or a wireless network. Furthermore, as described above with reference to FIG. 2, the image display apparatus 200 may receive Doppler data together with a Doppler image. Furthermore, the image display apparatus 200 may generate a Doppler image based on Doppler data received from outside.

In an operation S325, the image display apparatus 200 loads an acquired Doppler image. In other words, corresponding to the operation S320 in which the ultrasound medical apparatus 100 generates a Doppler image, the image display apparatus 200 loads a stored Doppler image. According to an embodiment of the present invention, the image display apparatus 200 may generate a Doppler image based on acquired Doppler data and load the Doppler image in the operation S325.

In an operation S330, the image display apparatus 200 displays a Doppler image. In other words, the image display apparatus 200 displays a Doppler image to diagnose a target body by using the Doppler image.

Operations S340 through S360 thereafter are as described above with reference to FIG. 3. In other words, the image display apparatus 200 may acquire a guideline based on a user input or an automatic detection algorithm and may determine a moving direction of a target body based on at least one of color information of a Doppler image and Doppler data and the guideline. Meanwhile, in the operation S340, unlike the ultrasound medical apparatus 100 described above with reference to FIG. 3, the image display apparatus 200 may determine a moving direction of a target body based on color values of a Doppler image. Furthermore, the image display apparatus 200 may display one or more first markers, which are 2-dimensionally or 3-dimensionally rendered, in the operation S360.

In other words, the image display apparatus 200 may determine a Doppler direction based on at least one of color values, which are information regarding colors displayed in a Doppler image, and Doppler data and may determine a moving direction of a target body by using the Doppler direction and the guideline. The embodiment in which the image display apparatus 200 determines a Doppler direction according to color value ranges is same as the embodiment described above with reference to FIG. 2.

Figure 6:
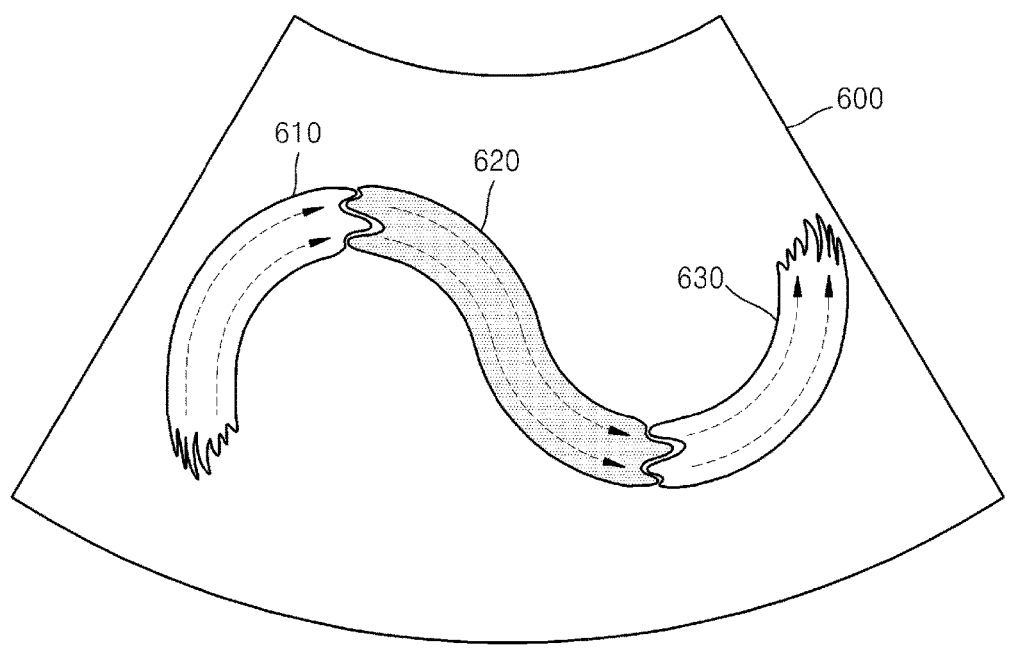
FIG. 6 is a diagram showing an example Doppler image.

FIG. 6 is a diagram showing an example Doppler image. FIG. 6 shows a Doppler image 600 showing movement of blood (that is, a blood flow Doppler image or a color Doppler image). The radial Doppler image 600 shown in FIG. 6 is generated as a probe located above the Doppler image 600 emits ultrasound signals. Meanwhile, although embodiments of the present invention are described with reference to FIGS. 6 through 10 by using a blood flow Doppler image showing flow of blood, a target body is not limited thereto. The target bodies of Doppler images may be tissues, and thus Doppler images may also include tissue Doppler image.

The Doppler image 600 shown in FIG. 6 may include a first region 610 in which blood gets close to a probe (that is, a location above the Doppler image 600), a second region 620 in which blood gets far from the probe, and a third region 630 in which blood gets close to the probe again. In the first region 610, the second region 620, and the third region 630, arrows for indicating direction in which blood moves are displayed, where the second region 620 is shaded differently to indicate a direction opposite to the direction indicated by the first region 610 and the third region 630.

Figure 7:
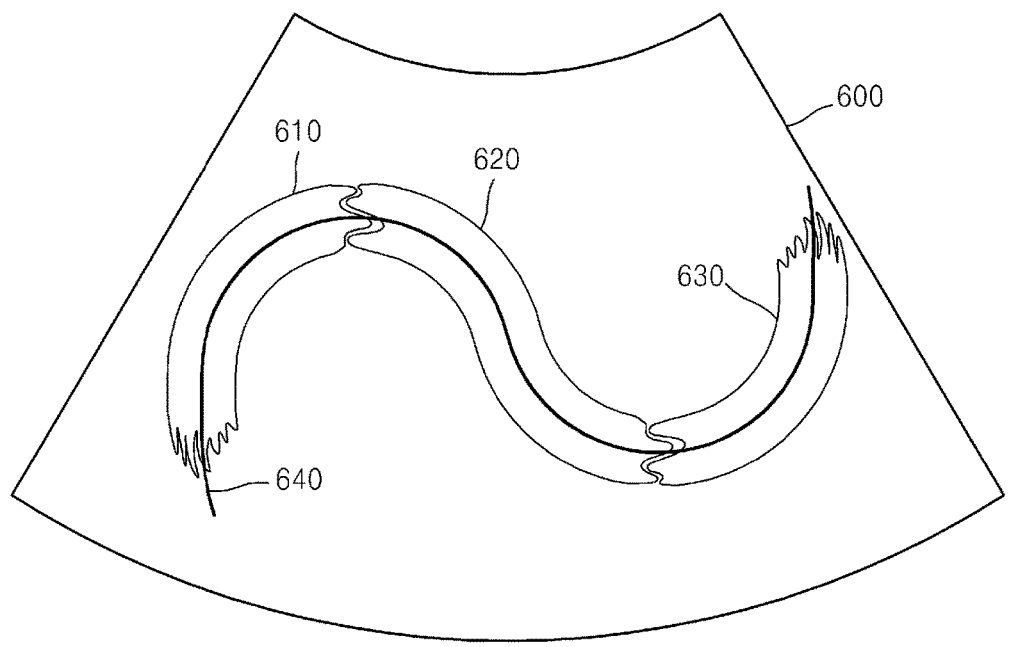
FIG. 7 is a diagram showing an embodiment of displaying a guideline.

FIG. 7 is a diagram showing an embodiment of displaying a guideline. FIG. 7 shows a guideline 640 that is either automatically generated by an automatic detection algorithm stored in the ultrasound medical apparatus 100 or the image display apparatus 200 or generated based on a user input.

In FIG. 7, the guideline 640 is displayed along a blood vessel in which a target body, that is, blood flows. Meanwhile, although the guideline 640 is shown as a single curved line in FIG. 7, shape of the guideline 640 is not limited thereto. In other words, the guideline 640 may have any of various shapes including a dotted line, a broken line, or more than one curved lines.

Figure 8A:
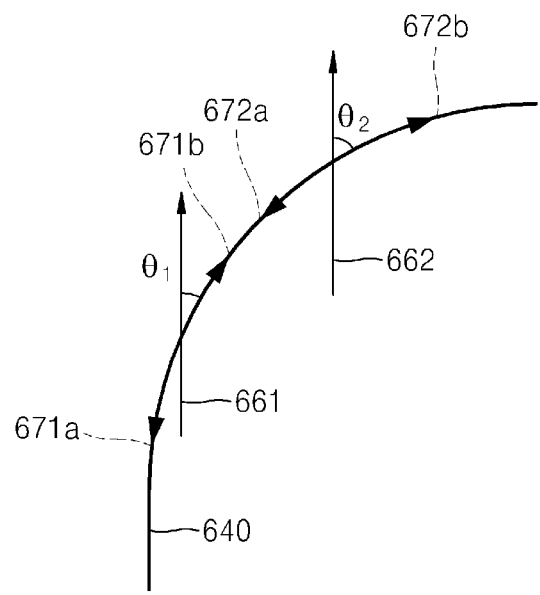
FIGS. 8A and 8B show an embodiment for determining a moving direction of a target body by using a Doppler direction based on Doppler data and a guideline.
Figure 8B:
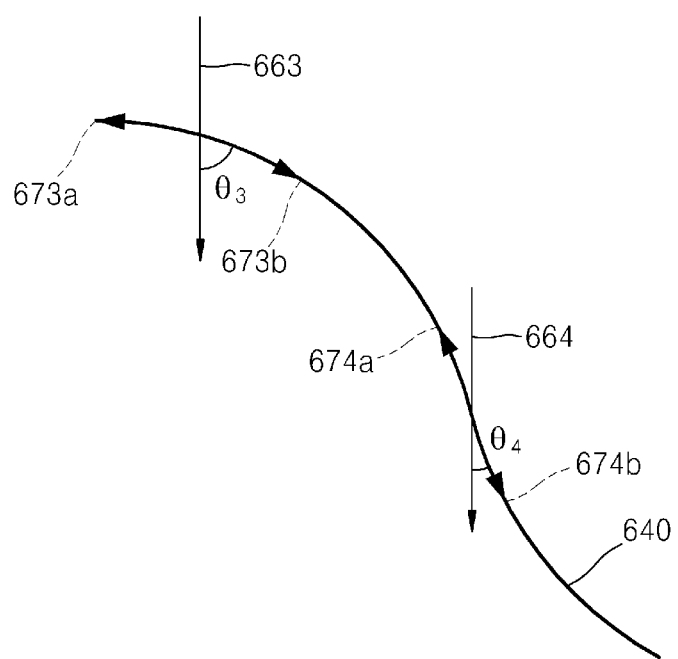

FIG. 8 shows an embodiment for determining a moving direction of a target body by using a Doppler direction based on Doppler data and a guideline. FIG. 8A shows the first region 610 of FIG. 7 in closer detail, whereas FIG. 8B shows the second region 620 of FIG. 7 in closer detail.

First, referring to FIG. 8, a process for determining a Doppler direction will be described. As described above with reference to FIG. 1, the ultrasound medical apparatus 100 may determine a Doppler direction by using symbolic elements or numeric elements included in Doppler data. For example, in case of a direction 661 of FIG. 8A, the ultrasound medical apparatus 100 may determine that a Doppler direction is a second direction toward a probe based on the symbolic element "–" included in Doppler data.

On the contrary, in case of a direction 662 of FIG. 8A, the ultrasound medical apparatus 100 may determine that a Doppler direction is a second direction toward a target body based on a numeric element (e.g., "86") included in Doppler data. In the same regard, in case of directions 663 and 664 of FIG. 8B, the ultrasound medical apparatus 100 may determine that a Doppler direction is a first direction away from a probe based on the symbolic element "+" or the numeral element "200" included in Doppler data. Meanwhile, Doppler direction corresponding to symbolic elements or numeric elements may be reversed. In other words, the symbolic element "+" may correspond to a second direction.

Alternatively, the image display apparatus 200 may determine a Doppler direction based on color information regarding a Doppler image, as described above with reference to FIG. 2. In other words, In other words, if value of a color displayed in a Doppler image is within a predetermined range of values corresponding to red color, the image display apparatus 200 may determine the direction 661 or the direction 662 of FIG. 8A as the direction toward the probe (the second direction). On the contrary, if value of a color displayed in a Doppler image is within a predetermined range of values corresponding to blue color, the image display apparatus 200 may determine the direction 663 or the direction 664 of FIG. 8B as the direction away from the probe (the first direction). Similar to a case regarding Doppler data, the relationships between color values and Doppler directions may be reversed.

Once a Doppler direction is determined based on Doppler data or color value, the ultrasound medical apparatus 100 and the image display apparatus 200 determine a moving direction of a target body based on the guideline 640 and the Doppler direction. According to the embodiment described above, the ultrasound medical apparatus 100 and the image display apparatus 200 may determine a direction, in which the guideline extends and an acute angle is formed between the direction and the Doppler direction, as the moving direction.

In detail, in case of the direction 661, the guideline 640 extends in two directions, that is, a direction 671a and a direction 671b. Meanwhile, the ultrasound medical apparatus 100 and the image display apparatus 200 may determine the direction 671b, in which the guideline 640 extends and an acute angle θ1 is formed between the direction and the Doppler direction 661, as the moving direction of the target body.

In the same regard, in case of the direction 662, the guideline 640 extends in two directions 672a and 672b, and the ultrasound medical apparatus 100 and the image display apparatus 200 may determine the direction 672b, in which the guideline 640 extends and an acute angle θ2 is formed between the direction and the Doppler direction 662, as the moving direction of the target body.

In the same regard, in case of the directions 663 and 664, the ultrasound medical apparatus 100 and the image display apparatus 200 may determine the directions 673b and 674b, in which the guideline 640 extend and acute angles θ3 and θ4 are respectively formed between the directions and the Doppler directions 663 and 664, as the moving directions of the target body.

Meanwhile, embodiments for determining a moving direction of a target body are not limited to the embodiment shown in FIG. 8, and the ultrasound medical apparatus 100 and the image display apparatus 200 may determine a moving direction of a target body based on Doppler data and the guideline 640 according to various other methods and algorithms.

Meanwhile, as described above with reference to FIGS. 1 and 2, the ultrasound medical apparatus 100 and the image display apparatus 200 may determine a moving direction of a target body by using statistical functions. Hereinafter, an embodiment in which the ultrasound medical apparatus 100 and the image display apparatus 200 utilizes statistical functions will be described in detail.

According to an embodiment of the present invention, the ultrasound medical apparatus 100 and the image display apparatus 200 may use statistical functions regarding various factors included in Doppler data. Factors included in Doppler data may include at least one from among a Doppler direction based on symbolic elements or numeric elements, moving speed, amplitude of a Doppler signal, power of a Doppler signal, and a distance to a nearby space, for example. As described above, various types of statistical functions may be utilized, e.g., average, sum, weighted sum, variance, average deviance, etc.

Hereinafter, embodiments regarding sum and weighted sum will be described. The ultrasound medical apparatus 100 and the image display apparatus 200 may determine a moving direction of a target body in consideration of not only Doppler data regarding an arbitrary location of the target body of which a moving direction is to be determined, but also Doppler data regarding a space nearby the location. Hereinafter, a location regarding which a moving direction of a target body is to be determined and a space nearby the location will be referred to as a 'region of interest (ROI).' A ROI may include not only a space 2-dimensionally adjacent to a location in four directions, but also a space 3-dimensionally adjacent to the location.

First, an embodiment regarding sum will be described. The ultrasound medical apparatus 100 and the image display apparatus 200 may determine a moving direction of a target body by simply summing Doppler data regarding one or more locations included in a ROI. For example, the ultrasound medical apparatus 100 and the image display apparatus 200 may determine a Doppler direction value "+1 (direction toward a probe)," "−1 (direction away from the probe)," or "0 (no data)," based on symbolic elements or numeric elements. Next, the ultrasound medical apparatus 100 and the image display apparatus 200 may sum the plurality of Doppler direction values regarding the plurality of locations and utilize a result thereof to determine a moving direction of a target body.

According to another embodiment regarding sum, the ultrasound medical apparatus 100 and the image display apparatus 200 may determine a Doppler direction by summing a plurality of values respectively obtained by multiplying a plurality of Doppler directions regarding a plurality of locations included in a ROI by a moving speed. In other words, if a Doppler direction is indicated by "+1," "−1," or "0" and a moving speed is indicated by "v," the ultrasound medical apparatus 100 and the image display apparatus 200 may obtain values "+v," "−v," and "0" by multiplying the respective direction elements by the moving speed. Next, the ultrasound medical apparatus 100 and the image display apparatus 200 may sum results of multiplications regarding the plurality of locations included in the ROI and utilize the sum for determining a moving direction of a target body.

An embodiment regarding weighted sum will be described below. The 0 and the image display apparatus 200 may obtain values regarding a plurality of locations included in a ROI by multiplying Doppler directions (+1, −1, or 0), moving speed v, and power p of Doppler signals. In other words, the ultrasound medical apparatus 100 and the image display apparatus 200 obtain one from among values "+v*p", "−v*p", and "0" with respect to each of a plurality of locations and may determined a Doppler direction regarding a ROI by summing all values regarding locations included in the ROI. In other words, the ultrasound medical apparatus 100 and the image display apparatus 200 may obtain a value indicating that the Doppler direction is a direction toward a probe if the sum of values is a positive value, may obtain a value indicating that the Doppler direction is a direction away from the probe if the sum of the values is a negative value, and may obtain a value indicating that a Doppler direction cannot be determined if the sum of the values is zero or a value within a predetermined range with which a Doppler direction cannot be determined.

According to another embodiment of the present invention, the ultrasound medical apparatus 100 and the image display apparatus 200 may calculate a statistical function by using a distance from the center of the ROI or a distance d to a space nearby a location at which a moving direction is to be determined. In other words, the ultrasound medical apparatus 100 and the image display apparatus 200 may determine a moving direction by summing a plurality of values, each of which is "+v*p", "−v*p", or "0", with respect to the ROI.

As described above, the ultrasound medical apparatus 100 and the image display apparatus 200 may determine a moving direction based on various factors including a Doppler direction included in Doppler data, moving speed, amplitude of a Doppler signal, power of the Doppler signal, and a distance to a nearby space. Furthermore, the ultrasound medical apparatus 100 and the image display apparatus 200 may utilize any of various statistical functions, and the functions stated above are merely examples thereof.

FIG. 9 is a diagram showing an embodiment of displaying a first marker, which indicates a moving direction, in a Doppler image. The ultrasound medical apparatus 100 and the image display apparatus 200 may display the at least one first marker 650 indicating a moving direction of a target body as described above with reference to FIG. 8 in the Doppler image 600.

Figure 9A:
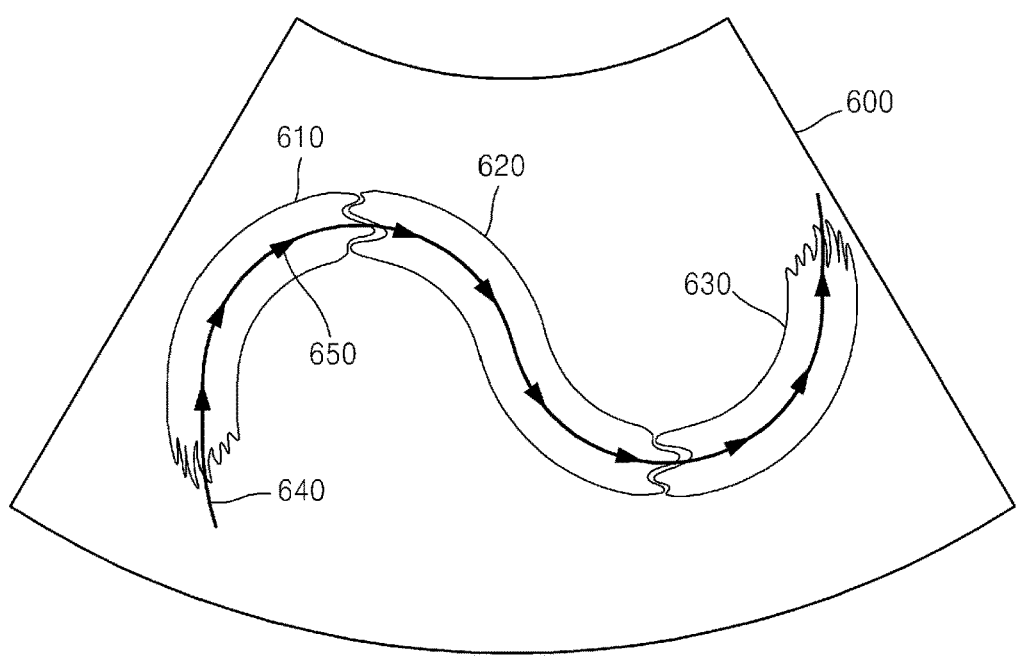
FIGS. 9A and 9B are diagrams showing an embodiment of displaying a first marker, which indicates a moving direction, in a Doppler image.

According to the embodiment shown in FIG. 9A, the ultrasound medical apparatus 100 and the image display apparatus 200 may display the at least one first marker 650 in the Doppler image 600 along the guideline 640. Displaying the at least one first marker 650 along the guideline 640 means not only that the center of the first marker 650 is precisely located on the guideline 640, but also that the first marker 650 is displayed within a predetermined distance from the guideline 640. In other words, unlike in FIG. 9, if the ultrasound medical apparatus 100 and the image display apparatus 200 display two parallel curves as the guidelines 640, the first marker 650 may be located between the two curves. In other words, the ultrasound medical apparatus 100 and the image display apparatus 200 may display the first marker 650 along the guideline 640 in any of various manners.

Furthermore, in FIG. 9A, the ultrasound medical apparatus 100 and the image display apparatus 200 may display the two or more first markers 650 along the guideline 640 at a predetermined interval. The ultrasound medical apparatus 100 and the image display apparatus 200 may adjust the interval between the two or more first markers 650 based on a user input or in-system. Furthermore, the shape of the first marker 650 is not limited to the triangular shape shown in FIG. 9, and the ultrasound medical apparatus 100 and the image display apparatus 200 may display the first marker 650 in various sizes, shapes, lengths, widths, brightness, and colors. In other words, the ultrasound medical apparatus 100 and the image display apparatus 200 may display various types of the first markers 650 for indicating a moving direction of a target body.

Figure 9B:
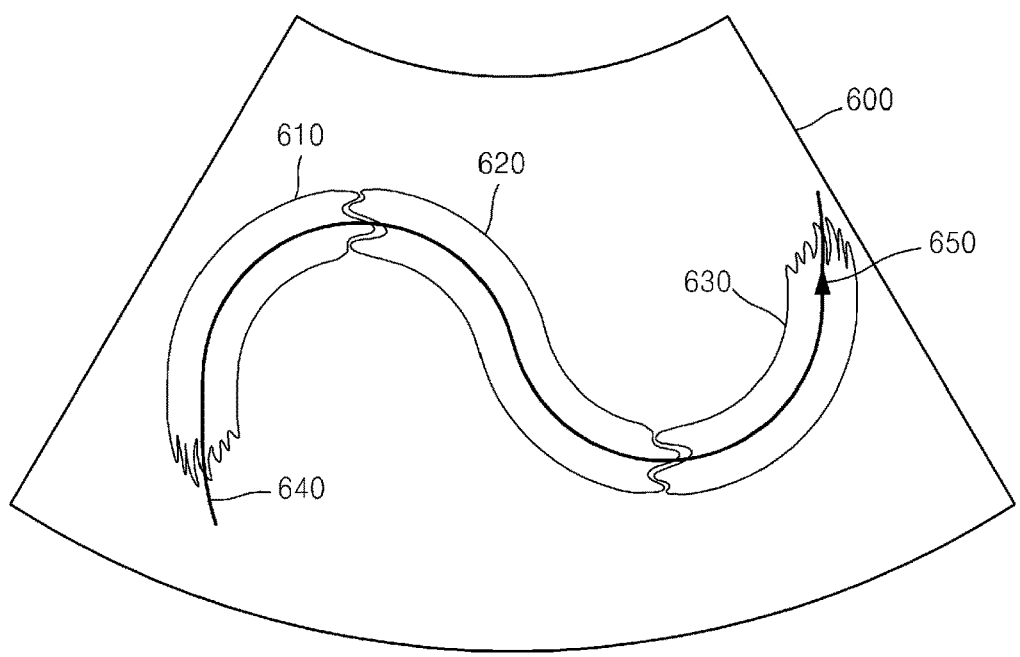

In FIG. 9B, the ultrasound medical apparatus 100 and the image display apparatus 200 display the first marker 650 at an end of the guideline 640. In other words, the ultrasound medical apparatus 100 and the image display apparatus 200 may display the one first marker 650 at an end of the guideline 640 to indicate a moving direction of a target body.

FIG. 10 is a diagram showing an embodiment of displaying a first marker, a second marker, and a third marker in a Doppler image. Here, the Doppler image shown in FIGS. 10A through 10D is different from the Doppler image shown in FIGS. 6 through 9, and a first region 710 and a second region 720 shown in FIGS. 10A through 10D are different from the first region 610 and the second region 620 shown in FIGS. 6 through 9. The Doppler image shown in FIG. 10 includes the first region 710 corresponding to the second direction in which blood flows toward a probe and the second region 720 corresponding to the first direction in which blood flows away from the probe. In other words, in FIG. 10, blood flows in at the lower-left portion of the first region 710 and flows out at the lower-right portion of the second region 720 (that is, in the clockwise direction in FIG. 10).

Figure 10A:
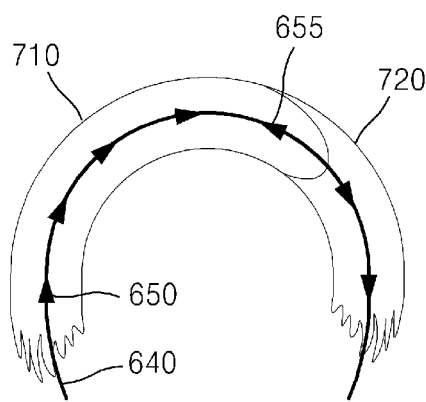
FIGS. 10A-10D are diagrams showing an embodiment of displaying a first marker, a second marker, and a third marker in a Doppler image.

In FIG. 10A, the ultrasound medical apparatus 100 and the image display apparatus 200 may receive input of the guideline 640 and display the guideline 640. Next, the ultrasound medical apparatus 100 and the image display apparatus 200 determines a moving direction of blood, which is the target body, in consideration of either Doppler data (in case of an ultrasound medical apparatus) or color values of a Doppler image (in case of an image displaying apparatus) together with the guideline 640 and displays the one or more first markers 650 in the Doppler image.

Meanwhile, a marker 655 indicates a direction different from the blood-flowing direction indicated by the first marker 650. In other words, Doppler data and color values regarding a location at which the marker 655 is displayed include symbolic elements, numeric elements, and color values indicating a direction toward a probe. Therefore, the marker 655 indicates the counter-clockwise direction, which is opposite to the clockwise direction corresponding to an end of the guideline 640. The inconsistency of directions may occur due to irregular turbulence of blood or structure of a target body shown in a Doppler image.

Figure 10B:
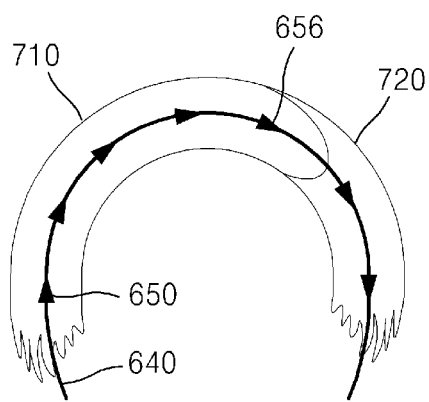

In FIG. 10B, the ultrasound medical apparatus 100 and the image display apparatus 200 displays the direction corresponding to the marker 655 of FIG. 10A as the clockwise direction corresponding to an end of the guideline 640. In other words, the ultrasound medical apparatus 100 and the image display apparatus 200 may display the marker 655 in a direction based on percentage of the marker 655 corresponding to a direction faced by an end of the guideline 640 with respect to the first markers 650. In other words, the ultrasound medical apparatus 100 and the image display apparatus 200 may change the marker 655 to marker 656 and display the marker 656. Therefore, even if flow of a portion of a target body is displayed in opposite direction, the ultrasound medical apparatus 100 and the image display apparatus 200 may precisely display information regarding the overall movement of the target body.

Figure 10C:
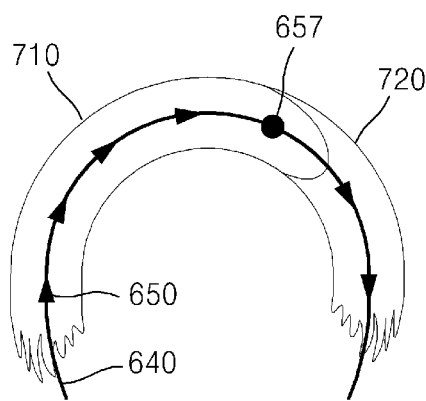

In FIG. 10C, the ultrasound medical apparatus 100 and the image display apparatus 200 displays a second marker 657 indicating that a direction is not consistent at the location of the marker 655 of FIG. 10A. In other words, instead of forcefully displaying the marker 655 to indicate the same direction as the at least one first markers 650, the ultrasound medical apparatus 100 and the image display apparatus 200 may indicate the opposite direction by using the second marker 657 distinguished from the first marker 650. Therefore, the ultrasound medical apparatus 100 and the image display apparatus 200 may precisely display information indicating that a target body includes a portion moving in a direction opposite to the direction in which the overall target body moves and location of the portion.

Figure 10D:
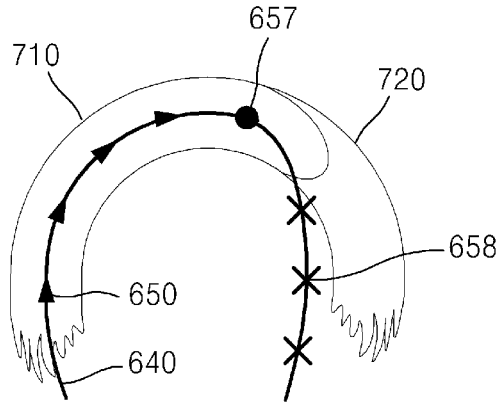

FIG. 10D shows a case in which the guideline 640 is generated at a location apart from a target body. In FIG. 10D, the ultrasound medical apparatus 100 and the image display apparatus 200 are unable to obtain Doppler data and color values at a location where the guideline 640 is apart from the first region 710. Therefore, the ultrasound medical apparatus 100 and the image display apparatus 200 are unable to determine a moving direction of a target body. Therefore, the ultrasound medical apparatus 100 and the image display apparatus 200 may display a third marker 658, which indicates that a moving direction is not determined, at a location where Doppler data and/or a color value is not obtained.

Therefore, a user of the ultrasound medical apparatus 100 and the image display apparatus 200 may precisely diagnose movement of a target body by relocating the guideline 640 or inputting the new guideline 640.

Meanwhile, FIG. 10D also shows the second marker 657 indicating an inconsistent direction as described above with reference to FIG. 10C. The first marker 650, the second marker 657, and the third marker 658 shown in FIG. 10 are merely examples, and the ultrasound medical apparatus 100 and the image display apparatus 200 may display the first marker 650, the second marker 657, and the third marker 658 in any of various forms.

Figure 11:
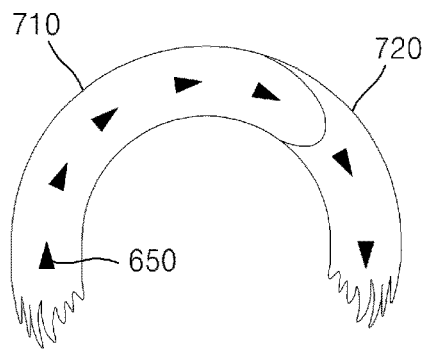
FIG. 11 is a diagram showing an embodiment of displaying at least one first marker in a Doppler image.

FIG. 11 is a diagram showing an embodiment of displaying at least one first marker in a Doppler image. Like in the embodiment described above with reference to FIG. 10, the ultrasound medical apparatus 100 and the image display apparatus 200 may display the at least one first marker 650 indicating a moving direction of a target body.

Meanwhile, in FIG. 11, the ultrasound medical apparatus 100 and the image display apparatus 200 do not display a guideline and indicates a moving direction by using the first marker 650 only. In other words, the ultrasound medical apparatus 100 and the image display apparatus 200 obtain a guideline based on a user input or an automatic detection algorithm. Furthermore, the ultrasound medical apparatus 100 and the image display apparatus 200 determines a moving direction in consideration of at least one of Doppler data and color values together with the guideline. However, the ultrasound medical apparatus 100 and the image display apparatus 200 do not display the guideline and display the at least one first marker 650 only. In other words, the guideline is used only for determining a moving direction and may either be displayed transparently to be invisible or not be displayed after being used in a system.

Figure 12:
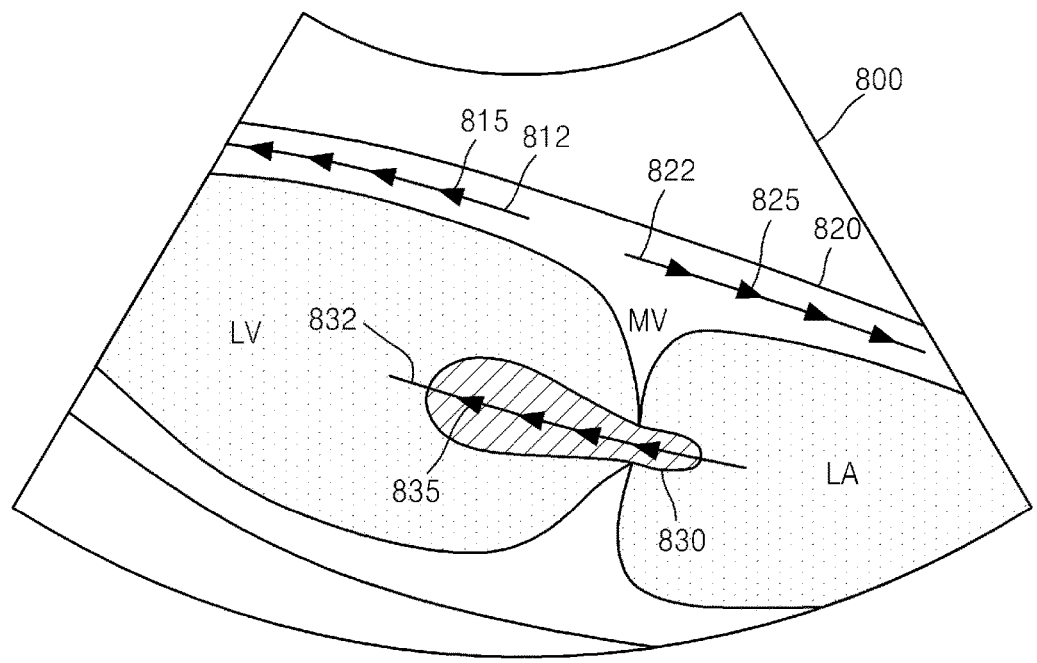
FIG. 12 is a diagram showing an embodiment of displaying markers in a case where color Doppler data and tissue Doppler data are simultaneously displayed.

FIG. 12 is a diagram showing an embodiment of displaying markers in a case where color Doppler data and tissue Doppler data are simultaneously displayed. In the embodiment shown in FIG. 12, the ultrasound medical apparatus 100 and the image display apparatus 200 display the ultrasound image 800 of the heart. The ultrasound image 800 of FIG. 12 shows a left atrium LA, a left ventricle, and a mitral valve, where the dark region 830 in FIG. 12 indicates blood flowing from the left atrium LA to the left ventricle LV as the left atrium LA contracts. As a heart muscle 820 surrounding the left atrium LA moves in the downward direction of the ultrasound image 800, the left atrium LA contracts. Meanwhile, a heart muscle surrounding the left ventricle LV expands in the upward direction of the ultrasound image 800 as the left ventricle LV expands Meanwhile, the ultrasound image 800 shown in FIG. 12 may include at least one of color Doppler data and tissue Doppler data. In other words, the ultrasound medical apparatus 100 and the image display apparatus 200 may display both color Doppler regarding blood flow and tissue Doppler regarding tissues. For example, the dark region 830 may be a Doppler image based on color Doppler data, whereas regions corresponding to the heart muscles surrounding the left atrium LA and the left ventricle LV may include tissue Doppler images based on tissue Doppler data. In other words, the ultrasound medical apparatus 100 and the image display apparatus 200 may determine moving directions of blood flow and heart muscles by using obtained color Doppler data and obtained tissue Doppler data. In the embodiment of FIG. 12, the blood flow shown in the dark region 830 moves in a direction toward a probe.

The ultrasound medical apparatus 100 and the image display apparatus 200 obtain guidelines 812, 822, and 832 based on a user input or automatic detection algorithm. In other words, the ultrasound medical apparatus 100 and the image display apparatus 200 may generate the guidelines 812, 822, and 832 to a moving direction of a target body and display the guidelines 812, 822, and 832 on a display screen. Meanwhile, unlike as shown in FIG. 12, the ultrasound medical apparatus 100 and the image display apparatus 200 may use the guidelines 812, 822, and 832 only for determining a moving direction of a target body and may display the guidelines 812, 822, and 832 transparent on a display screen or may not display the guidelines 812, 822, and 832 on a display screen.

Next, the ultrasound medical apparatus 100 and the image display apparatus 200 may determine Doppler direction of a target body (a direction toward a probe or a direction away from the probe) by using at least one of color information of a Doppler image and Doppler data and may determine a moving direction of the target body by using the Doppler direction and guidelines.

According to an embodiment of the present invention, the ultrasound medical apparatus 100 and the image display apparatus 200 may determine a moving direction of a target body by using statistical functions regarding at least one from among symbolic components of the target body, numeric components of the target body, moving speed of the target body, amplitude of a Doppler signal, power of the Doppler signal, and a distance to a nearby space. In other words, as described above with reference to FIGS. 1 and 2, the ultrasound medical apparatus 100 and the image display apparatus 200 may determine a moving direction of the target body by using statistical functions including sum, weighted sum, average, variance, etc. regarding various factors and may also consider Doppler data of a nearby space close to an arbitrary location of a target body to determine the moving direction of the target body.

Next, the ultrasound medical apparatus 100 and the image display apparatus 200 displays first markers 815, 825, and 835 indicating moving directions of blood flow and heart muscles in the ultrasound image 800. In other words, the ultrasound medical apparatus 100 and the image display apparatus 200 may display the first markers 815, 825, and 835 along the guidelines 812, 822, and 832 or at a predetermined interval. As described above, the ultrasound medical apparatus 100 and the image display apparatus 200 may not display the guidelines 812, 822, and 832 and may display the first markers 815, 825, and 835 only.

Figure 13:
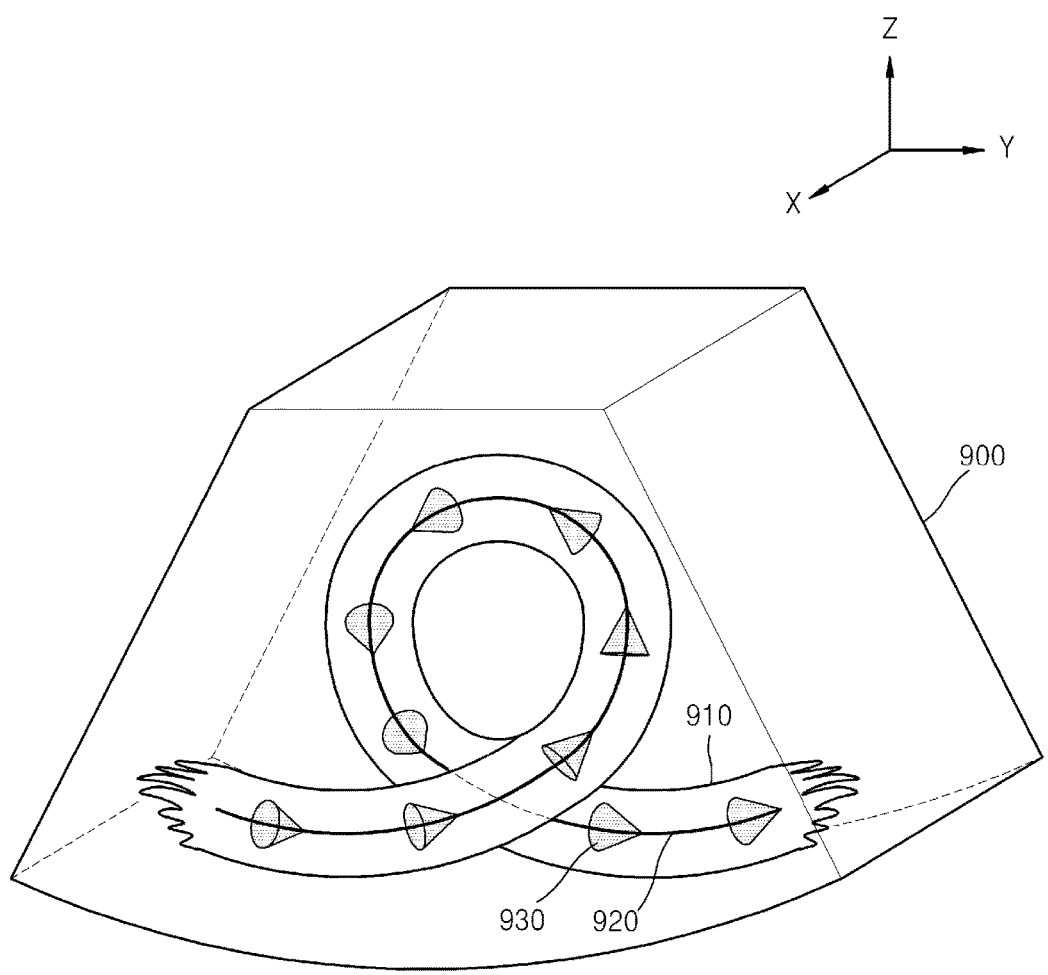
FIG. 13 is a diagram showing an embodiment for displaying a 3D marker in an ultrasound image.

FIG. 13 is a diagram showing an embodiment for displaying a 3D marker in an ultrasound image 900. In the embodiment shown in FIG. 13, the ultrasound medical apparatus 100 and the image display apparatus 200 displays a 3D ultrasound image 900 including a blood vessel 910, that is, volume data.

Meanwhile, in the embodiment shown in FIG. 13, blood flows from the left to the right. In other words, blood flows from the left of the blood vessel 910 in the counterclockwise direction along the circular shape.

First, the ultrasound medical apparatus 100 and the image display apparatus 200 obtain 3D Doppler data regarding a target body. In other words, as described above with reference to FIG. 1, the ultrasound medical apparatus 100 and the image display apparatus 200 may obtain stereoscopic-spatial Doppler data, which is Doppler data regarding a 3D space.

Next, the ultrasound medical apparatus 100 and the image display apparatus 200 generates a 3D ultrasound image 900 or obtains the 3D ultrasound image 900 obtained from outside and displays the 3D ultrasound image 900 on a display screen. Furthermore, the ultrasound medical apparatus 100 and the image display apparatus 200 obtains a guideline 920 based on a user input or an automatic detection algorithm.

The ultrasound medical apparatus 100 and the image display apparatus 200 determines a moving direction of a target body by using 3D Doppler data, color values of a Doppler image, and the guideline 920. In other words, the ultrasound medical apparatus 100 and the image display apparatus 200 may determine a moving direction of a target body in consideration of various information regarding movement of the target body, such as symbolic components of the target body, numeric components of the target body, and colors, together with the guideline 920. Meanwhile, the ultrasound medical apparatus 100 and the image display apparatus 200 may determine a moving direction of a target body by using statistical functions regarding symbolic components of the target body, numeric components of the target body, moving speed of the target body, amplitude of a Doppler signal, and power of the Doppler signal. Detailed descriptions thereof are as given above with reference to FIG. 8.

The ultrasound medical apparatus 100 and the image display apparatus 200 display the determined moving direction by using 3D markers 930. The 3D markers 930 may display the moving direction of the target body in a 3D space. In other words, the ultrasound medical apparatus 100 and the image display apparatus 200 may determine a moving direction of a target body in a 3D space in consideration of both a guideline and a Doppler direction.

The 3D marker displayed at the leftmost portion of a blood vessel 910 indicates that a target body moves to the right and in a direction opposite to the x-axis direction of FIG. 9 at the same time. Next, as it gets closer to the center portion of the blood vessel 910, 3D markers gradually move in the x-axis direction (that is, an outward direction). The ultrasound medical apparatus 100 and the image display apparatus 200 may display movement of a target body in a 3D space by using the 3D markers 930. In the same regard, the 3D markers displayed to the right of the blood vessel 910 indicate that the target body moves to the right and in the x-axis direction of FIG. 9 at the same time.

To display a moving direction of a target body in a 3D space, the ultrasound medical apparatus 100 and the image display apparatus 200 may 3-dimensionally render the 3D markers 930 and may display the processed 3D markers 930.

FIG. 14 is a diagram showing an embodiment for detecting a guideline based on an automatic detection algorithm. Although FIGS. 14A through 14D show a case in which a Doppler image 1000 is a 2D image, the present invention is not limited thereto, and the embodiment may also be applied to a 3D image using 3D Doppler data.

First, the process in which the ultrasound medical apparatus 100 and the image display apparatus 200 obtains a guideline 1030 by using an automatic detection algorithm will be briefly described below. First, the ultrasound medical apparatus 100 and the image display apparatus 200 determine regions including information regarding movement of a target body in the Doppler image 1000. Next, the ultrasound medical apparatus 100 and the image display apparatus 200 detect the guidelines 1030 from the determined regions. Various types of automatic detection algorithms may be applied to each of the two operations. Hereinafter, detection of the guideline 1030 according to an embodiment of the present invention will be described in detail.

Figure 14B:
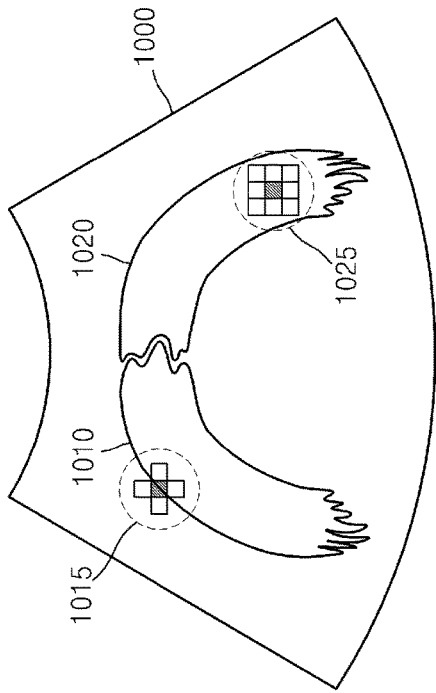
FIGS. 14A-14D are diagrams showing an embodiment for detecting a guideline based on an automatic detection algorithm.
Figure 14D:
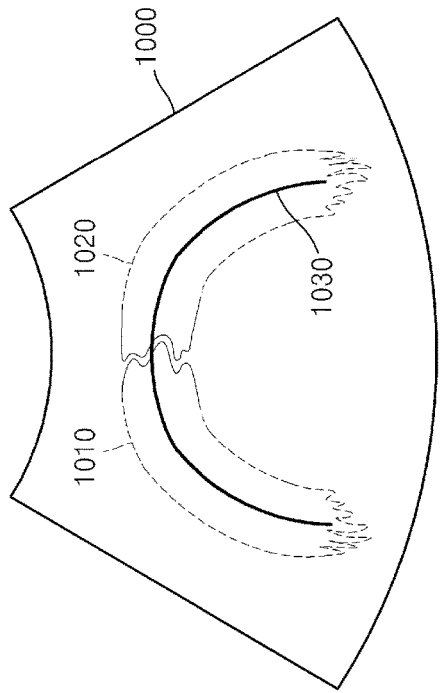
Figure 14A:
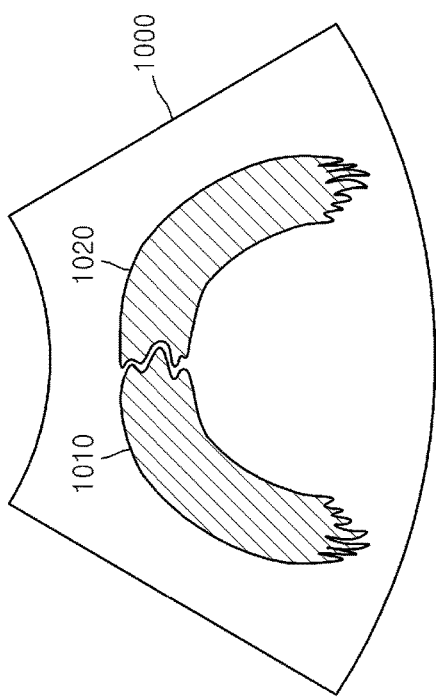

In FIG. 14A, the ultrasound medical apparatus 100 and the image display apparatus 200 display the Doppler image 1000 including a first region 1010 and a second region 1020 based on obtained Doppler data. In other words, the dark regions, that is, the first region 1010 and the second region 1020 indicate moving target bodies. In FIG. 14B, the ultrasound medical apparatus 100 and the image display apparatus 200 analyze the Doppler data based on the connected component analysis (CCA) algorithm. In other words, the ultrasound medical apparatus 100 and the image display apparatus 200 determine the first region 1010 and the second region 1020 based on whether spatially connected components include Doppler data with respect to a pixel or a pixel group of a predetermined size.

In FIG. 14B, the ultrasound medical apparatus 100 and the image display apparatus 200 applies 4-CCA algorithm with respect to a pixel group 1015. In other words, the ultrasound medical apparatus 100 and the image display apparatus 200 analyze Doppler data corresponding to locations that are adjacent to a dark pixel (or a dark pixel group) in the pixel group 1015 in four perpendicular directions. The ultrasound medical apparatus 100 and the image display apparatus 200 may store a result of analysing the dark pixel as a predetermined value.

In FIG. 14B, the ultrasound medical apparatus 100 and the image display apparatus 200 may apply 8-CCA algorithm to a pixel group 1025. The ultrasound medical apparatus 100 and the image display apparatus 200 may analyze not only Doppler data corresponding to pixels adjacent to the dark pixel (or the dark pixel group) in four perpendicular directions, but also Doppler data corresponding to pixels adjacent to the dark pixel (or the dark pixel group) in four diagonal directions.

Therefore, the ultrasound medical apparatus 100 and the image display apparatus 200 may distinguish the first region 1010 and the second region 1020, which are regions including Doppler data regarding the Doppler image 1000, from other regions including no Doppler data.

Figure 14C:
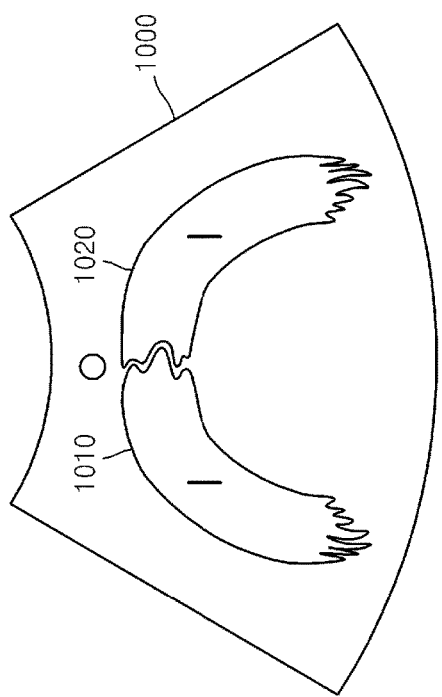

In FIG. 14C, the ultrasound medical apparatus 100 and the image display apparatus 200 displays a result of analyzing the Doppler image 1000 by using values "1," and "0." In other words, the ultrasound medical apparatus 100 and the image display apparatus 200 may store a result of analyzing the Doppler image 1000 by using the CCA algorithm, where the ultrasound medical apparatus 100 and the image display apparatus 200 may store the value "1" for the first region 1010 and the second region 1020 including Doppler data and may store the value "0" for the other regions.

In other words, the ultrasound medical apparatus 100 and the image display apparatus 200 may obtain information regarding a region in which movement of a target body is detected by performing a masking operation with respect to the Doppler image 1000.

In FIG. 14D, the ultrasound medical apparatus 100 and the image display apparatus 200 extracts the guideline 1030 by using the skeletonization algorithm. In other words, the ultrasound medical apparatus 100 and the image display apparatus 200 may obtain the guideline 1030 regarding the first region 1010 and the second region 1020 including Doppler data.

Meanwhile, the ultrasound medical apparatus 100 and the image display apparatus 200 may obtain the guideline 1030 by using not only the skeletonization algorithm, but also the morphology operation algorithm. In other words, user input unit 120 may detect the guideline 1030 by repeatedly applying at least one of the dilation algorithm for zooming in the first region 1010 and the second region 1020 and the erosion algorithm for zooming out the first region 1010 and the second region 1020.

According to another embodiment of the present invention, the ultrasound medical apparatus 100 and the image display apparatus 200 may detect the longest path included in the first region 1010 and the second region 1020 including Doppler data and determine the longest path as the guideline 1030. In other words, if changes of shapes of regions including Doppler data are not significant, the ultrasound medical apparatus 100 and the image display apparatus 200 may determine the longest path in a determined region as the guideline 1030.

The automatic detection algorithms described above with reference to FIGS. 14A through 14D are merely examples of algorithms used for obtaining guidelines, and one of ordinary skill in the art will understand that guidelines may be obtained by using any of various other algorithms.

According to the ultrasound medical apparatus 100, the image display apparatus 200, the method of displaying ultrasound images, and the method of displaying images, movements of target bodies, such as blood flows or movements of tissues, may be easily recognized by displaying markers indicating moving directions of the target bodies. In other words, a user of a device may intuitively recognize a moving direction of a target body. Therefore, a Doppler image may be analyzed conveniently and efficiently, and thus the efficiency of diagnosing a patient may be improved.

Therefore, even an unskilled user or a patient not familiar with an ultrasound image may easily understand and analyze a Doppler image. Therefore, problems in the related art including misrecognition of color information of Doppler image as a vein or an artery and difficulty of recognizing a Doppler image. Therefore, Doppler images may become more popular.

Furthermore, for comparison with vector Doppler indicating blood flow or movements of tissues, the methods and the apparatuses described above enables easy recognition of a target body without an additional hardware. Furthermore, compared to the vector Doppler indicating blood flow or movement of a tissue, the method and the apparatus described above enable easy recognition of movement of a target body without additional hardware. Furthermore, the method and the apparatus described above may be applied to even a probe with a small aperture, e.g., a phased array probe, regardless of hardware configuration. Therefore, movement of a target body may be intuitively and easily inferred and recognized based on movement in a direction regarding a probe indicated by markers.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound medical apparatus comprising:
a hardware processor which generates a Doppler image from Doppler data regarding a target body received from an ultrasound probe coupled to the ultrasound medical apparatus, acquires a guideline regarding at least one of the Doppler data and the Doppler image, and generates a plurality of first markers each indicating a moving direction of the target body at a different respective location of the target body, wherein the hardware processor determines the moving direction based on the guideline and the Doppler data; and
a display coupled to the hardware processor, which displays the plurality of first markers each indicating the moving direction of the target body at the respective location based on the guideline and the Doppler data,
wherein the hardware processor determines a percentage of the generated first markers indicating a direction opposite to a direction towards a first end of the guideline and, if the determined percentage is below or equal to a predetermined percentage, the hardware processor generates a second marker indicating an inconsistent direction at a location of a first marker indicating the opposite direction and the display displays the second marker, and
wherein the hardware processor determines whether the moving direction of the target body is determined based on the guideline and the Doppler data and, upon determining that the moving direction of the target body cannot be determined based on the guideline and the Doppler data, the hardware processor generates a third marker indicating that the moving direction of the target body is not determined, relocates the guideline, and determines the moving direction of the target body based on the relocated guideline and the Doppler data, and the display displays the third marker and relocated guide line, and wherein the hardware processor generates the Doppler image to include a blood flow Doppler image showing flow of blood and a tissue Doppler image showing movement of a tissue, specifies a plurality of regions including at least one region having flow of blood in the Doppler image and including at least another region having movement of the tissue in the Doppler image based on the automatic detection algorithm, acquires a plurality of guidelines for the plurality of regions, and determines the moving direction of the flow of blood and of the movement of the tissue for the plurality of regions based on the plurality of guidelines and the Doppler data.

2. The ultrasound medical apparatus of claim 1, wherein the display displays the guideline in the Doppler image.

3. The ultrasound medical apparatus of claim 1, wherein the hardware processor acquires the guideline based on a user input for drawing a line in the Doppler image or an automatic detection algorithm stored in advance.

4. The ultrasound medical apparatus of claim 1, wherein the hardware processor determines the moving direction of the target body based on a Doppler direction of the target body, which is determined based on symbolic elements or numeric elements of the Doppler data, and the guideline.

5. The ultrasound medical apparatus of claim 4, wherein the hardware processor determines a direction, in which the guideline extends and an acute angle is formed between the direction and the Doppler direction, as the moving direction.

6. The ultrasound medical apparatus of claim 4, wherein the hardware processor determines the moving direction of the target body based on statistical functions regarding at least one from among the Doppler direction, a moving speed of the target body, amplitudes of Doppler signals, power of the Doppler signals, and distances to nearby spaces.

7. The ultrasound medical apparatus of claim 6, wherein the statistical function is a function using Doppler data of a nearby space to a location at which the moving direction of the target body is to be determined.

8. The ultrasound medical apparatus of claim 1, wherein the display unit displays the plurality of first markers along the guideline.

9. The ultrasound medical apparatus of claim 1, wherein the display unit displays the plurality of first markers at a predetermined interval.

10. The ultrasound medical apparatus of claim 1, wherein the display unit displays one of the plurality of first markers at a first end of the guideline.

11. The ultrasound medical apparatus of claim 1, wherein the Doppler data comprises 2D Doppler data or 3D Doppler data.

12. The ultrasound medical apparatus of claim 1, wherein the hardware processor 2-dimensionally renders or 3-dimensionally renders the first marker, and the display unit displays the rendered first marker.

13. The ultrasound medical apparatus of claim 1, wherein the display displays the plurality of first markers after changing at least one from among length, size, width, contrast, and color of the first marker, based on the Doppler data.

* * * * *